(12) United States Patent
Alvarez et al.

(10) Patent No.: US 10,953,240 B2
(45) Date of Patent: Mar. 23, 2021

(54) OCULAR DEVICES

(71) Applicant: ALVALUX MEDICAL, Hermalle-sous-Argenteau (BE)

(72) Inventors: Michel Alvarez, Hermalle-sous-Argenteau (BE); Denis Flandre, Brussels (BE)

(73) Assignee: ALVALUX MEDICAL, Liège (BE)

( * ) Notice: Subject to any disclaimer, the term of this patent is extended or adjusted under 35 U.S.C. 154(b) by 178 days.

(21) Appl. No.: 15/781,499

(22) PCT Filed: Dec. 5, 2016

(86) PCT No.: PCT/EP2016/079765
§ 371 (c)(1),
(2) Date: Jun. 5, 2018

(87) PCT Pub. No.: WO2017/097708
PCT Pub. Date: Jun. 15, 2017

(65) Prior Publication Data
US 2018/0264284 A1    Sep. 20, 2018

(30) Foreign Application Priority Data

Dec. 9, 2015   (EP) .................................... 15198641

(51) Int. Cl.
*A61N 5/06*         (2006.01)

(52) U.S. Cl.
CPC ......... *A61N 5/0622* (2013.01); *A61N 5/0618* (2013.01); *A61N 2005/0626* (2013.01); *A61N 2005/0648* (2013.01); *A61N 2005/0651* (2013.01); *A61N 2005/0659* (2013.01);
(Continued)

(58) Field of Classification Search
CPC .................................................... A61N 5/0622
See application file for complete search history.

(56) References Cited

U.S. PATENT DOCUMENTS

| 2012/0199995 A1 | 8/2012 | Pugh et al. |
| 2014/0277291 A1* | 9/2014 | Pugh ........................ G02C 7/04 607/88 |
| 2014/0379054 A1 | 12/2014 | Cooper et al. |

(Continued)

FOREIGN PATENT DOCUMENTS

| EP | 2778752 A2 | 9/2014 |
| WO | WO2010122434 A1 | 10/2010 |

OTHER PUBLICATIONS

European Patent Office search report dated Feb. 20, 2017 re PCT Application No. PCT/EP2016/079765 of Alvalux Medical.

*Primary Examiner* — Allen Porter
(74) *Attorney, Agent, or Firm* — Daugherty & Del Zoppo Co. LPA

(57) ABSTRACT

Ocular devices are provided for placement in the upper fornix of the eye and having a body that encompasses a low-level light source, an energy source, a microcontroller, and an antenna for delivering a programmable, fade in-out, light therapy regimen to treat neurological and ophthalmic diseases and disorders. In one embodiment the ocular device delivers a programmable green light therapy to reduce elevated intraocular pressure (IOP) and retinal hypoxia during the nocturnal period, that is, when these risk factors are at their highest level especially in glaucoma, age-related macular degeneration and diabetic retinopathy patients.

25 Claims, 14 Drawing Sheets

(52) U.S. Cl.
CPC ............. *A61N 2005/0662* (2013.01); *A61N 2005/0663* (2013.01)

(56) References Cited

U.S. PATENT DOCUMENTS

| | | | |
|---|---|---|---|
| 2016/0045760 A1* | 2/2016 | Tapper | A61N 5/0616 607/90 |
| 2016/0317834 A1* | 11/2016 | Kirk | A61N 5/0613 |
| 2018/0256906 A1* | 9/2018 | Pivonka | A61N 2/006 |
| 2019/0076669 A1* | 3/2019 | Alvarez | A61N 5/0616 |

\* cited by examiner

OCULAR DEVICES

FIELD OF THE INVENTION

The present invention relates to improvements in or relating to ocular devices and is more particularly concerned with wearable ocular devices for delivering light energy to the eye.

BACKGROUND OF THE INVENTION

It is estimated that 114 million people will suffer from glaucoma, 288 million from age-related macular degeneration (AMD), and 224 million from diabetic retinopathy (DR) by 2040. Incidence increases rapidly with age and among certain populations.

With glaucoma, continued intraocular pressure (IOP) elevation above 22 mm Hg is regarded as a major risk factor, and, may result in progressive and irreversible deterioration of the optic nerve, leading to blindness. IOP is usually most elevated and sustained during sleep thereby leading to further damage or deterioration of the optic nerve. Patients at risk of glaucoma would rather not be subjected to a lifetime of eye-drop medication (of which approximately 50% do not adhere to the regime after the first few weeks for various reasons including side effects) or surgery (given the trauma and potential complications).

With AMD and DR, hypoxia (lack of adequate oxygen supply) to the retina (and especially during sleep when oxygen demand increases as the retina adapts to darkness) has been implicated as a major risk factor for disease progression leading to blindness. As a result of retinal hypoxia, the eye increases its angiogenic activity (creates new, yet fragile, blood vessels) to supply more oxygen to the retina but these vessels are prone to leakage thus impairing vision. There have been significant advances in the management of AMD and DR with the introduction of anti-angiogenesis drugs delivered by a needle injection to the vitreous (posterior segment of eye) However, these treatments are in-clinic, invasive, expensive, difficult to obtain in many countries, and carry risks of devastating complications (e.g. endophthalmitis and retinal detachment) to less severe complications (e.g. elevated IOP and inflammation).

While much focus in recent years for the treatment of glaucoma, AMD, DR and other diseases have been on drugs which face side effects, varying levels of efficacy, and resulting lack of adherence and/or non-invasive and invasive surgical options which also have varying degrees of safety and efficacy and reduced patient interest given the potential for adverse events, patients and doctors are always interested in other preventive, first-line, non-toxic, non-invasive, safe, convenient, home-based therapy solutions, either as a stand-alone treatment or in combination with other therapies (as is often the case with diseases which are difficult to treat), and which can be delivered during sleep hours.

Therefore, there have been advances toward ocular insert technologies to deliver drugs more conveniently to improve patient adherence and outcomes. One such ocular insert device is described in U.S. Pat. No. 8,679,078 in which a drug delivery device is configured for being positioned on the sclera of the eye. However, these advances still face toxic and systemic effects since, in most cases, they simply use existing drugs which are incorporated into a slow release ocular carrier for convenience.

The use of light therapy is known for the treatment of symptoms such as seasonal affective disorder (SAD). US-A-2014/0277291 and US-A-2012/0199995 disclose a contact lens, configured to be positioned on and over a tear film layer of the cornea of a user, which delivers a light therapy regimen. Such devices need to be configured to the shape of the corneal surface of the eye in a similar way to conventional contact lenses which correct for myopia (short-sightedness), hyperopia or hypermetropia (long-sightedness) and astigmatism or a combination thereof. As a result, each device needs to be customized to each user or a group of users having similar corneal dimensions.

U.S. Pat. No. 8,764,185 also discloses an eye-mountable device having an inwardly facing light source, the device being configured to be positioned on a corneal surface overlaying a pupil. Such a device is effectively a contact lens which needs to be customized for each user.

Light therapy has also been researched as an effective treatment for IOP reduction in glaucoma, and for retinal hypoxia inhibition in AMD and DR. Conventional light therapy normally requires a patient to sit with their eyes "open" at a prescribed distance from the bulky, non-portable, energy inefficient light source such as a light box. Many patients (and their household members) find this therapy burdensome and inconvenient, especially when they share the same room. As a result of the above issues, more proximal to eye, light-emitting devices have been developed, for example, eye headsets, goggles or visors, which have improved on portability but these devices are still quite bulky, can be uncomfortable with extended wear time, are non-discrete, and generally not pleasing aesthetically. In addition, these devices still require the patient to have an open eye or open eyes and are useless during sleep.

More recently, eye-masks that do not require the eye (or eyes) to be open, such as, light-emitting sleep masks (eg. Noctura 400 from Polyphotonix Medical headquartered in Sedgefield, United Kingdom), deliver light therapy through closed eyelids for the treatment of DR and diabetic macular oedema. These sleep masks are still considered rigid, bulky, uncomfortable, un-natural, and are energy inefficient as the amount of light necessary to pass effectively through the dampening effect of the eyelid tissue is significant (e.g. up to 99% of the light energy does not pass through the closed eyelid). While these masks are designed to radiate approximately 100× the light energy necessary in order to overcome the eyelid dampening effect, they can cause a potential problem for the up to 20% of the patient population that suffer from lagophthalmos (i.e. when eyelids remain partially open during sleep). This condition creates a window to allow much greater amounts of unwanted light (i.e. an overdose) emitting from the mask to reach retina thus causing discomfort, awakening, restless sleep, and other adverse events. Masks that are designed to press actively on the eyelid (to help keep the eyelids shut) raise other significant issues including pain, discomfort and a sustained increase in IOP (a leading risk factor for glaucoma especially with an aging, at-risk population).

New methods and approaches are therefore desirable to deliver light energy therapy directly to the eye and its surrounding structures, for example, under a closed eye in a convenient sleep cycle, in a more direct/proximal, energy efficient, convenient/ambulatory, hidden/aesthetically pleasing, and controlled manner.

Whilst so-called "smart" contact lenses may be used in the future, these devices still face many issues related to form, fit, comfort, safety, tolerability and aesthetics as they cover and interface with the highly sensitive and innervated cornea. (In fact, the cornea has the highest nerve density of all organs in the body at 300-600 times greater than skin, making any injury to the structure excruciatingly painful).

Published studies from the first glaucoma-related smart contact lens to market (SENSIMED Triggerfish® by Sensimed AG, Lausanne Switzerland) reported adverse events including: inflammation of the cornea (keratitis), blurred vision and/or cornea remodeling, sensor pressure mark, corneal abrasion, discomfort/irritation, and corneal erosion. Corneal structure, topography, and dimensions (e.g. diameter, radius of curvature, and eccentricity) vary greatly across patients (compared with the vastly more uniform sclera) making it very challenging for a 'one-size fits all' or generic fit smart contact lens especially as it contains microelectronics resulting in a thicker, more rigid and costly device compared to the thin, soft, conforming, relatively inexpensive, hydrogel contact lenses popular in today's market.

There is therefore a need to provide ocular devices which overcome the issues with presently used devices.

SUMMARY OF THE INVENTION

It is an object of the present invention to provide an ocular device which can provide light energy to an eye under a closed eyelid without causing significant discomfort to a user.

In accordance with one aspect of the present invention, there is provided an ocular device configured to be worn on a scleral surface of an eye of a user, the device comprising:

a body component;

at least one light source component mounted in the body component and configured for providing light energy to an eye;

a microcontroller component mounted in the body component and configured for controlling the operation of at least the light source component;

an antenna component at least partially mounted in the body component and connected to the microcontroller component, the antenna component being configured for at least receiving external signals and for passing them to the microcontroller component; and at least one energy source component configured for supplying power to at least the light source component and the microcontroller component.

By providing a small ocular device which can easily be correctly positioned to direct and distribute light into an eye of a user, the benefits of light therapy can readily be realized without the disadvantages of the prior art systems. In particular, due to the small overall size and thickness of the ocular device, it is comfortable to wear during the day as well as at night.

In one embodiment, at least one flexible printed circuit board is provided in the body component. At least one of said at least one light source component, the microcontroller component, and said at least one energy source component are configured to be mounted on said at least one flexible printed circuit board.

In a preferred embodiment, the at least one flexible printed circuit board comprises a plurality of sections which are hinged relative to one another. In one implementation, the plurality of sections comprises a central section and two side sections. The side sections may be similarly dimensioned and symmetrically arranged on either side of the central section. Alternatively, one side section may have different dimensions to the other side section and each section is arranged on either side of the central section.

In one embodiment, the ocular device comprises a substantially hollow ring extension which extends from the body component. The ring extension may comprise a waveguide configured for directing light energy from said at least one light source.

Such a ring extension has the advantage that more light can be directed into the eye as the ring extension extends downwards from the body component and around the corneal limbus when in position.

The ring extension may further comprise the antenna component. By mounting the antenna component within the ring extension, a larger, more efficient, coil can be formed for providing inductive coupling with external sources for the transfer of data to and from the microcontroller component. In addition, the antenna component may be used for collecting external energy and supplying internal energy for powering the components of the ocular device either directly or by way of a rechargeable battery.

In one embodiment, the antenna component is mounted on said at least one flexible printed circuit board.

In another embodiment, the energy source component is mounted within the body component and comprises at least one thin-film rechargeable micro-battery. This has the advantage of providing a compact self-contained device.

In a further embodiment, the energy source component is external to the body component and is configured to couple with the antenna component to provide energy thereto for powering said at least one light source component and the microcontroller component.

In a preferred embodiment, the ocular device further comprises a sensor component mounted on said at least one flexible printed circuit board in the body component. Typically, such a sensor comprises an accelerometer which determines the movement of the eye when the device is being worn as well as determining if it is being worn at all. However, other sensors for detecting if the device is being worn on the eye requiring less energy than an accelerometer, for example, a strain gauge configured for sensing a small deformation of the device body or sense the pressure of the eyelid. Such a strain gauge may also be configurable to detect changes or patterns related to intraocular pressure (IOP) to help with diagnosing and treating glaucoma.

Other sensor components may include an osmolarity sensor (based on electrical impedance or light absorbance) for measuring the quality of the tear film, for example, excessive levels of salinity and protein concentration (i.e. hyperosmolarity) on the surface of the eye to help with diagnosing and treating dry eye syndrome, and, an image sensor (e.g. complementary metal-oxide-semiconductor or CMOS device) for recording the changing morphology of the Meibomian gland (i.e. meibography) over a period of time to help with understanding, diagnosing and treating dry eye syndrome.

Whilst it is preferred that the light source component(s) operates at certain wavelengths, such light components may comprise one of the following: at least one solid-state light emitting diode, at least one organic light-emitting diode; at least one quantum dot light-emitting diode; a phosphorescent light source; a chemiluminescent light source; and strontium aluminate nanoparticles.

The main wavelength range is in the blue-green area of the visible portion of the electromagnetic spectrum, typically in a wavelength range of 430 nm to 590 nm. A luminous flux up to 10 lm may be used.

In one embodiment, the light source component is programmable. In this embodiment, the light source component can be controlled to operate in accordance with a predetermined programme including duration (e.g. millisecond pulses), intensity, frequency of operation, wavelength etc.

In an embodiment, the light source component is configured to focus light, when in-situ on the eye, onto the cornea and retina thereof. In contrast to known smart contact lenses, the light is focussed in an indirect manner onto the cornea and thence to the retina of the eye. As the light source is not located on the cornea surface to directly focus light into cornea, its innovative working principle relies on "indirect" light-guiding to retina.

The microcontroller component may comprise a wireless module configured for communicating wirelessly with an external controller, the external controller being configured for at least programming the microcontroller to control the light source. In one embodiment, the external controller is configured for controlling at least one of: the wavelength, light patterns (including binary code), duration of the light (including millisecond pulses), and luminosity of the light generated by the light source component.

In another embodiment, the light source component emits light in a wavelength range of between 620 nm and 3000 nm, that is, in the red-infrared region of the electromagnetic spectrum. In this embodiment, the light is not directed into the eye but towards the Meibomian gland in the eyelid to warm it thereby freeing and releasing more meibum to improve tear film production.

In an embodiment, the antenna component interfaces with a recharger station and is configured to recharge the energy source component.

At least one further sensor component configured to measure the luminance of the light source component may be provided. The microcontroller component may include a memory component which is configured to store data measured by the at least one sensor component.

In one embodiment, the ocular device further comprises at least one additional sensor component configured for monitoring parameters indicative of at least one of: use and performance of the device, and physiological conditions of the eye. Such an additional sensor component may comprise an accelerometer or a strain gauge for determining movement of the device when in use.

It is preferred that the body component comprises a soft, flexible, conforming, biocompatible material that encompasses all components of the device. In one embodiment, the biocompatible material comprises silicone rubber. In another embodiment, the body component has its outer surface treated with an anti-microbial coating.

In order to direct light from the light source component more efficiently, the body component may include at least one portion which comprises a solid screen for at least inhibiting light from passing through that portion. Alternatively or in addition, the body component may include at least one surface coated with a reflector mirror film.

The body component may comprise at least one photovoltaic cell portion for energy harvesting of ambient light. Each photovoltaic cell portion may comprise a connection with the energy source component which may be used to recharge the energy source component.

In one embodiment, the body component comprises at least one kinetic energy harvesting cell connected to the energy source component. By harvesting kinetic energy, it is possible to recharge the energy source component.

In accordance with another aspect of the present invention, there is provided an ocular system comprising:—
an ocular device as described above; and
a recharger station for recharging the energy source component of the ocular device.

The recharger station may operate using near-field induction or radio frequency power transfer for recharging the energy source component in the ocular device. (If a photovoltaic cell is provided in the device body, the recharger may recharge the energy source component using light. Similarly, recharging of the energy source component may be achieved or complemented using kinetic energy, for example, by shaking, if a kinetic energy harvesting cell is present. Body heat of the user may also be used to recharge the energy source component, using thermal energy emissions, if a flexible thermoelectric generator (TEG), based on thermoelectric materials, is incorporated. It may also be understood that the energy source component in the ocular device may be entirely powered by one, or a combination of, light, kinetic and/or thermal energy harvesting.

In one embodiment, the recharger station comprises a storage container into which the ocular device is placed when not in use. In this embodiment, the storage container is further configured for programming the ocular device.

In another embodiment, the recharger station comprises a mini-charger control unit. In this embodiment, the mini-charger control unit may form part of an eye mask wearable by a user of the ocular device. Alternatively, the mini-charger control unit may form part of a spectacle frame or be attachable to the spectacle frame.

In accordance with a further aspect of the present invention, there is provided a method of reducing intraocular pressure and/or ocular hypertension, the method comprising:—
inserting an ocular device as described above onto an ocular conjunctiva of an eye and under an eyelid of a user; and
directing light into the eye of the user from the ocular device.

In accordance with yet a further aspect of the present invention, there is provided a method of reducing retinal hypoxia in the treatment of diabetic retinopathy, the method comprising:—
inserting an ocular device as described above onto an ocular conjunctiva of an eye and under an eyelid of a user; and
directing light into the eye of the user from the ocular device.

In accordance with another further aspect of the present invention, there is provided a method of reducing retinal hypoxia in the treatment of age-related macular degeneration, the method comprising:—
inserting an ocular device as described above onto an ocular conjunctiva of an eye and under an eyelid of a user; and
directing light into the eye of the user from the ocular device.

In accordance with yet another further aspect of the present invention, there is provided a method of treating seasonal affective disorder, the method comprising:—
inserting an ocular device as described above onto an ocular conjunctiva of an eye and under an eyelid of a user; and
directing light into the eye of the user from the ocular device.

In each of the methods of treatment described above, the method may further comprise programming the directed light to have a primary light spectrum peak in the blue-green region of the visible spectrum. In addition, the method may further comprise adjusting the light to have a retinal illuminance of up to 100 scotopic Td for a cyclical treatment time of up to 15 minutes per hour or for a continuous treatment time of up to 8 hours.

In yet another aspect of the present invention, there is provided a method of reducing Meibomian gland dysfunction, the method comprising:— inserting an ocular device as described above onto an ocular conjunctiva of an eye and under an upper eyelid of a user; and directing infrared radiation outwards from the ocular device towards the Meibomian gland in the upper eyelid of the user.

The ocular device of the present invention, together with its associated ocular system, provides many advantages over the prior art solutions for light therapy as will become apparent from the description below.

BRIEF DESCRIPTION OF THE DRAWINGS

For a better understanding of the present invention, reference will now be made, by way of example, to the accompanying drawings in which:—

DESCRIPTION OF THE INVENTION

Figure 1:
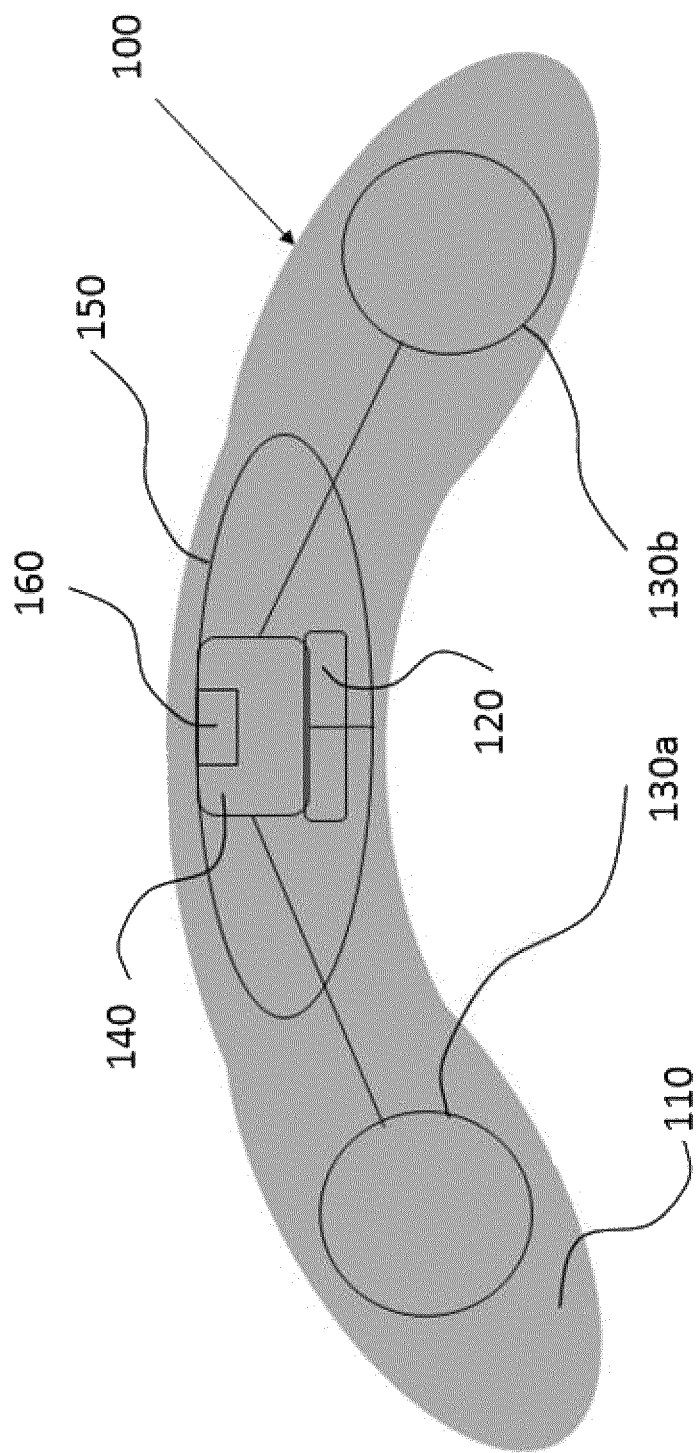
FIG. 1 illustrates a schematic front view of an ocular device for delivering light energy to an eye in accordance with a first embodiment of the present invention.

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes.

The present invention relates to ocular devices and methods used to deliver low-level energy (light) to treat diseases and disorders of the eye and surrounding structures. In particular, low-level light energy (radiant flux or luminosity) as low as 5 µW may be used, typically in a range of between 55 µW and 1005 µW. More specifically, the ocular device delivers a programmable green light therapy to reduce elevated intraocular pressure (IOP) in glaucoma or ocular hypertensive patients during the nocturnal period where IOP is generally highest. The programmable green light therapy may also reduce nocturnal retinal hypoxia in patients suffering from diabetic retinopathy (DR) and age-related macular degeneration (AMD). In addition, the ocular device may be used for the treatment of seasonal affective disorder (SAD) and circadian rhythm sleep disorders. Suitable wavelengths of electromagnetic radiation are used according to the particular treatment.

The term "light" as used herein is intended to refer mainly to visible light within the blue-green region of the electromagnetic spectrum but is also intended to include infrared (IR) radiation. Visible light is used to treat IOP, DR and AMD, for example, whilst IR is used to treat Meibomian gland dysfunction (MGD).

In one embodiment, a green light-emitting diode implemented in the ocular device of the present invention only needs up to 1 mW of electrical power to provide up to 100 µW of optical power to deliver the needed therapy for glaucoma, AMD, DR, etc. In some embodiments, only 100 µW of electrical power is required to provide 5 µW of optical power. The requirement for such low levels of electrical power and optical power enables miniaturization, remote power transfer and internal (or in-body) storage etc.

As the ocular device of the present invention is positioned on a scleral surface, such as, the sclera/conjunctiva of the eye (on the bulbar or ocular conjunctiva, or conjunctival sac), and not on the cornea, it is possible to make the device thicker than conventional contact lenses using different materials. In addition, the device only needs to be transparent or translucent in regions through or from which light is to be delivered to the eye (or to the photovoltaic cell), and it can be optimized for light propagation at the wavelengths to be used for light therapy.

Components or elements which are the same have the same reference numbers throughout the Figures.

In an embodiment illustrated in FIG. 1, a schematic front view of an ocular device 100 in accordance with the present invention is shown. The ocular device 100 comprises a housing or body component 110 in which a low-level light source 120 is mounted. At least one energy source 130a, 130b, a microcontroller 140, and an antenna 150 are also mounted within the housing 110. Although, two energy sources 130a, 130b are shown, it will readily be appreciated that a single energy source may be utilized.

Although the energy source component is described for supplying power to the other components within the ocular device, it will readily be appreciated that it can also collect energy, for example, from the antenna, a photovoltaic cell or an energy harvesting cell and store it. The energy source component therefore may also be used for both energy storage and power management, and, may be integrated with the microcontroller.

In addition, as mentioned above, the energy source component is to be coupled to the antenna irrespective of the location of the antenna as will be described in more detail below.

A sensor element 160, for example, in the form of an accelerometer, may also be provided. Such an element may form part of the microcontroller 140 (as shown) or may be a separate component within the housing or body component 110 but connected to the microcontroller for providing signals thereto in accordance with measurements taken. Other sensor elements, for example, temperature sensors and brightness sensors, may be implemented.

It will readily be appreciated that the accelerometer is not essential but is desirable to measure eye movement when a user is wearing the ocular device. In this way, the accelerometer provides signals which indicate a) whether the ocular device is being worn, and, b) whether the ocular device is being worn correctly. Other low cost, and low power sensor elements may be provided, for example, for measuring the luminance of the light source and changes during use (under eyelid conditions) as the upper eyelid acts as a reflector, or for measuring temperature to provide an indication when the device was being worn on eye. A strain gauge sensor could also be provided in the device to monitor the deformation of the device is in normal conditions and to determine that it is not overstressed.

Whilst sensing the movement of the eye is an indication of use of the ocular device, sensing the temperature of the device also provides an indication of the device being worn. Brightness (i.e. light) sensors may be used to ensure that the light is appropriate for the particular light therapy.

The housing 110 comprises a soft material. The soft material may be any moldable polymer that is above its glass transition temperature at 35 degrees C., and has naturally hydrophobic properties to prevent water ingress into the body of the device 100 thereby preventing damage to the internal components. Suitable materials include, for example, a soft, flexible, silicone rubber or acrylic elastomer. The outer surface of the housing 110 is preferably plasma treated to change the surface energy so that it becomes hydrophilic to improve adhesion to eye's surface via capillary action and/or may be treated with an antimicrobial coating which also provides for capillary action. Additionally, the housing 110 may have a portion (not shown) comprising a solid screen for at least inhibiting light from passing through that portion, and/or at least one surface coated with a reflector mirror film. Furthermore, the housing 110 may include at least one photovoltaic cell portion for energy harvesting of ambient light, each photovoltaic cell portion being connected to the energy source 130a, 130b.

In addition, the housing 110 has sufficient flexibility to be able to match or conform to the curvature of the scleral surface on which it is intended to be worn.

In one embodiment where visible light is implemented in the ocular device 100, the light source 120 is centrally located within the housing such that, when the ocular device 100 is worn on the eye by a user, the light shines toward the cornea to deliver light to the retina. A waveguide or lens (not shown) may be provided in the light source 120 which is configured for directing emitted light toward the cornea, through the pupil and onto the retina. Alternatively or in addition, the waveguide may be separate from the light source but optically connected thereto. Other optical elements may be used for directing the light more efficiently. Such optical elements may include gratings, cladding and optical fibers.

The light source 120 may comprise light-emitting diodes (LEDs), for example, solid-state LEDs, quantum dot LEDs (QLEDs), or organic LEDs (OLED), which are capable of emitting light in the visible part of the electromagnetic spectrum, for example, in the range of between 400 nm and 700 nm), preferably in the range associated with blue-green light, that is, between 430 nm and 590 nm range, and most preferably, in the range between 495 nm and 510 nm for delivering highly efficient green light during scotopic vision (that is, vision under low light conditions). Preferably, wavelengths in the range of 433 nm to 586 nm may be implemented with luminous flux values of up to 10 lm—preferably in a range between 0.001 lm and 1 lm.

It will readily be appreciated that the wavelength range implemented may be continuous within at least a portion of the abovementioned range, or may be discrete wavelength bands within the overall wavelength range with different wavelengths being used for different portions of the low-level light treatment.

In addition, phosphorescent and/or chemiluminescent materials or devices, including those containing strontium aluminate nanoparticles may be used as light sources. Strontium aluminate activated by europium, $SrAl_2O_4$:Eu(II):Dy(III), is a newer material with higher brightness and significantly longer glow persistence.

Waveguides may be used, for example, fiber optic guides, to distribute the light in an arcuate or circular manner relative to the cornea to provide a distributed illumination beside or around the cornea at the limbus so that the retina may receive up to 100 scotopic trolands (Td) of illumination. This will be described in more detail below with reference to FIGS. 2 and 3.

In one embodiment, the light source 120 may emit light in other regions of the electromagnetic spectrum, for example, in the full visible and infrared (IR) regions of the electromagnetic spectrum. Wavelengths of between 400 nm and 750 nm for visible and 750 nm and 100 μm for IR.

Emitting light in multiple wavelengths is possible with the use of multiple single color LEDS, bi-color LEDs (e.g. two dies with same leads antiparallel to one another where current flow in one direction emits one color and current in opposite direction emits another color) or tri-color LEDs (e.g. three dies with separate leads connected to the same die and a fourth lead for a common anode or cathode).

In an embodiment where IR radiation is used in the ocular device in accordance with the present invention, the IR radiation is directed away from the cornea and the retina towards the eyelids so as to warm Meibomian (or tarsal) glands in upper eyelids so that they secrete more meibum (and improve tear film) when treating MGD—the leading cause of evaporative dry eye disorder (also known as dry eye syndrome, keratoconjunctivitis sicca (KCS), dysfunctional tear syndrome, lacrimal keratoconjunctivitis, evaporative tear deficiency, aqueous tear deficiency and LASIK-induced neurotropic epitheliopathy (LNE)).

Hence, the light source 120 may be programmable to emit light at one or more predetermined wavelengths, for one or more predetermined durations (including millisecond pulses), in one of more predetermined directions, and for one or more predetermined luminosities in accordance with the light which is suitable for a user of the ocular device. In addition, the light source 120 may be configured to focus light, when in-situ on the eye, onto the cornea and retina thereof.

The microcontroller 140 is in electrical contact with the light source 120 and the energy source 130a, 130b so that it can be powered by the energy source, and, control and communicate the programmable therapy to the light source 120. The microcontroller 140 may comprise at least one micro-integrated circuit or micro-chip.

In one embodiment, the light source 120, the at least one energy source(s) 130a, 130b, the microcontroller 140, the antenna 150, and, sensor 160 (if present as described below) may be mounted on a single flexible printed circuit board (PCB). Such a PCB may comprise one or more sections and be configured to adjust to the curvature, within the housing 110, of the scleral surface on which the ocular device is to be worn as described in more detail below with reference to FIGS. 12 to 15.

The microcontroller 140 may comprise a wireless module configured for communicating wirelessly with an external controller, the external controller being configured for at least programming the microcontroller to control the light source 120. The external controller may control at least one of: the wavelength, light patterns (e.g. binary coded), duration of the light (e.g. millisecond pulses) and luminosity of the light generated by the light source 120.

The microcontroller 140 may include a memory for storing data measured by sensor elements until the ocular device is being recharged when a transfer of data can take place between the memory and an external device, for example, a computer platform such as a tablet, smartphone or laptop. Desktop computers can also be used.

The antenna 150 in electrical contact with the microcontroller 140 is used for wirelessly recharging the energy source 130a, 130b through near field induction or radio frequency (RF) power transfer. The antenna 150 also operates to transfer data between a remote base station or equipment (not shown) and the microcontroller 140. It will readily be appreciated that the data transferred may include a programmed therapy and patient adherence or wear time (to the microcontroller 140) and measurements taken by sensors, such as accelerometer, temperature or light measurements, in the ocular device (from the microcontroller 140). Remote base stations or equipment, for example, remote recording and/or monitoring devices, are described in more detail below.

In addition, or as an alternative to recharging the energy source component using RF power transfer, the energy source component may be recharged using light (using a photovoltaic cell in the device as described above), kinetic energy (as described below), and heat (using a thermoelectric generator (TEG) cell in the device).

Whilst TEG is possible, it depends on a temperature difference to be able to recharge the energy source component, and its location within the device may require the use of different materials to direct heat towards the eyelid (for dry eye as described above) and to retain heat from the eye. If one or more of these technologies is integrated, a smaller battery could be implemented for the energy source component hybridized with the technologies discussed above.

Whilst the antenna 150 may be mounted within the housing 110 may comprise a coil, other antenna types are also possible, for example, single metal wires for radio frequency (RF) coupling at frequencies between 900 MHz and 2.4 GHz which penetrate less into human tissue. Planar antennas comprising two metal plates could be used where one plate acts as a shield to prevent radiation being directed towards the eye as well as providing a reflector for the light source 120.

In an alternative embodiment to the ocular device 100 shown in FIG. 1, the ocular device may be powered wirelessly through inductive coupling (during light delivery sequence) so that the device does not contain an energy source (e.g. battery) but it would only incorporate the light source 120, the microcontroller 140, (sensor 160 if present), and the antenna 150. (In such case, a energy storage capacitor may be required instead of, or in addition to, the energy source). Such an embodiment is described in more detail below with reference to FIG. 3.

Figure 2:
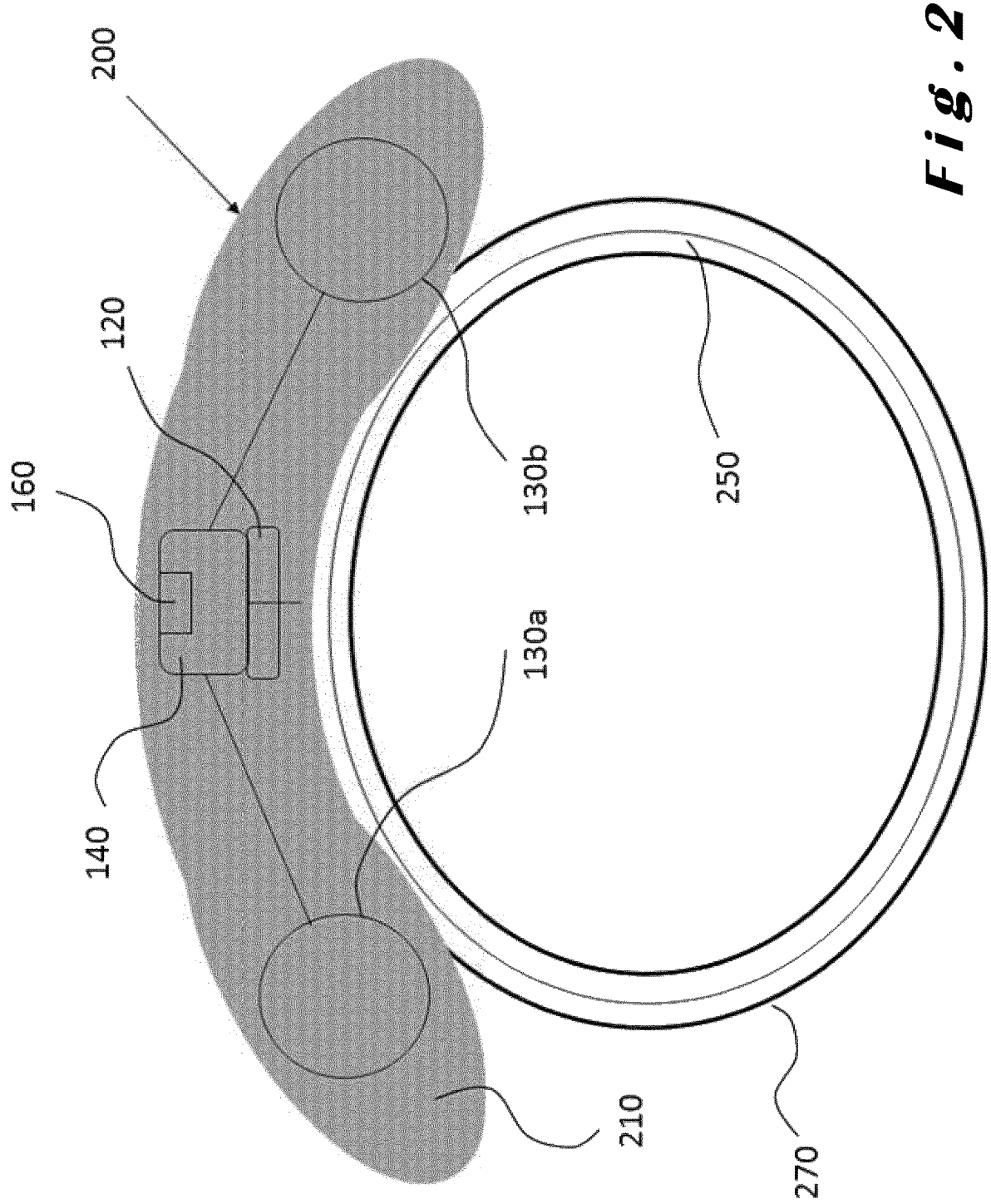
FIG. 2 illustrates a schematic front view of an ocular device for delivering light energy to an eye in accordance with a second embodiment of the present invention.

In another embodiment of the present invention, as shown in FIG. 2, an ocular device 200 comprises a housing or body component 210 to which is attached a hollow ring extension 270. The housing or body component 210 is similar to the housing 110 of the ocular device 100 but to which the ring extension 270 is attached. Components within the housing 210 are similar to those within the housing 110 and will not be described in detail again here. Instead of the microcontroller 140 connecting to an antenna 150 within the housing 110, the microcontroller 140 connects to an antenna 250 in the hollow ring extension 270.

The ring extension 270 is configured to be connected to housing 210 so that light from the central light source 120 is fed into the ring extension 270 and the light is transmitted around the ring extension providing a more uniform distribution of light to the eye. In use, the ring extension 270 sits outside the cornea on the bulbar or ocular conjunctiva at or beyond the corneal limbus of a user as will be described in more detail below.

The ring extension 270 comprises plastic fiber optic cable of up to 100 µm diameter to distribute the light around the corneal limbus. This 360-degree fiber optic "light ring" is further encapsulated by the same material (e.g. soft silicone) used in the housing of the ocular device as described above. This ring could serve to further stabilize ocular device while delivering light more efficiently and uniformly through cornea to retina.

By having a substantially circular antenna around the corneal limbus, coupling efficiency with remote devices is also facilitated and enables an energy source to be provided outside the ocular device on a wireless platform if needed. Such an embodiment is described below with reference to FIG. 3.

Figure 3:
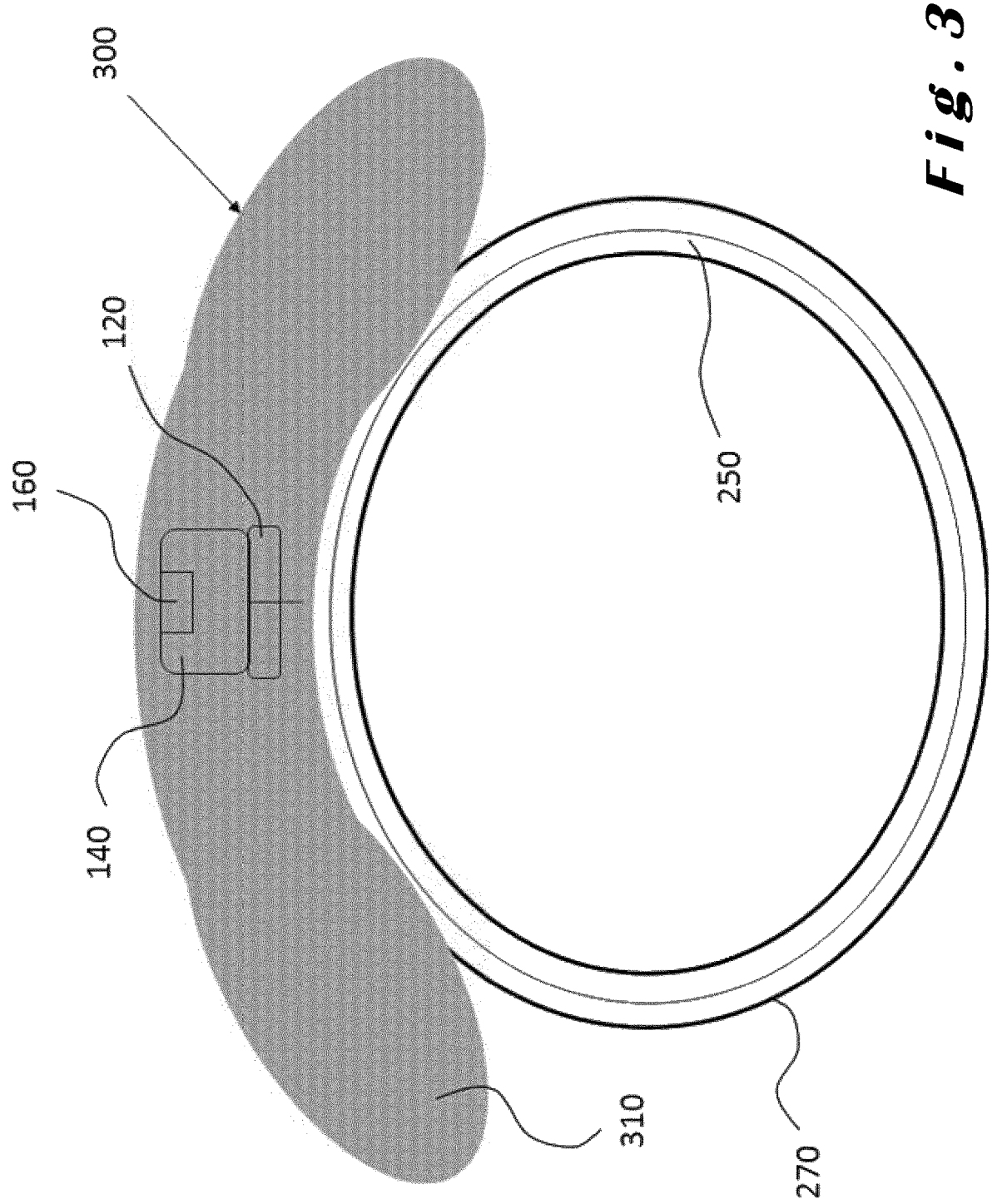
FIG. 3 illustrates a schematic front view of an ocular device for delivering light energy to an eye in accordance with a third embodiment of the present invention.

Turning now to FIG. 3, in this embodiment, the ocular device 300 is wirelessly inductively powered and controlled through the antenna 250 by a near-field energy source (e.g. rechargeable battery) with an attached exciter coil worn around or near the eye (e.g. headband with power source wired to soft eyepatch with coil) and a remote base unit (e.g. smartphone) worn by or placed near the patient.

In the embodiment of FIG. 3, whilst there is no internal energy source, an external energy source must be in the vicinity to ensure that sufficient power is available for powering the microcontroller 140, the sensor 160 (if present), and the light source 120. Operation of the ocular device 300 shown in FIG. 3 is described in more detail with reference to FIG. 9.

Figure 4:
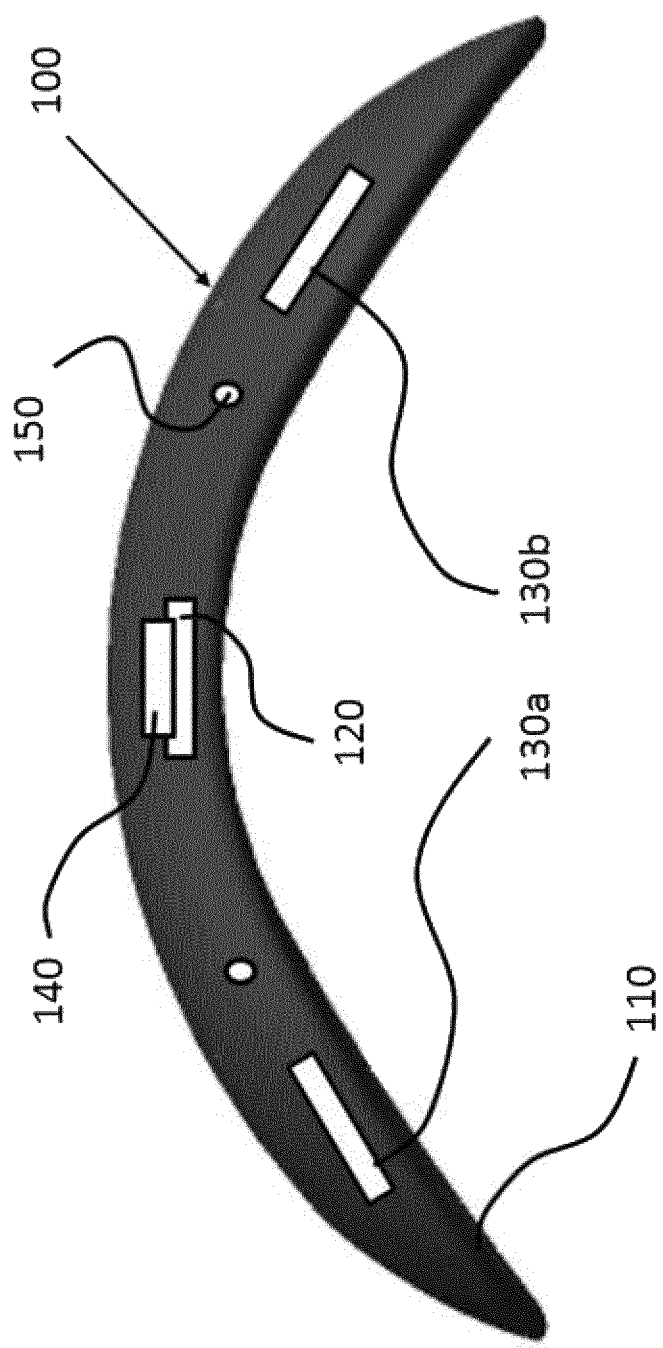
FIG. 4 illustrates a schematic side view of the embodiment shown in FIG. 1.

FIG. 4 illustrates a side view of the ocular device 100 shown in FIG. 1. As shown, the antenna 150 is in the plane of the ocular device 100 with the microcontroller 140 located on and connected to the central light source 120.

In one embodiment, the housing or body component of the ocular device is substantially bean-shaped, is symmetrical about a longitudinal axis, as described below with reference to FIGS. 12 to 14, and has typical dimensions of:

Length: 22 mm
Width: 7 mm at the center widening to 9.5 mm at the ends
Thickness: 1.5 mm
Base Radius: 12.5 mm The base radius corresponds to the average curvature of the human eye at the sclera (anterior surface or outermost surface) and is chosen to provide a good fit when the device is worn on the scleral surface of the eye. This is in contrast to a contact lens which typically has a base radius of curvature of between 7 mm and 9 mm.

Whilst examples of dimensions are given above, it will readily be appreciated that other suitable dimensions are possible, such as, a width between 8 mm and 10 mm with a thickness of up to 4 mm, and that the invention is not limited to the values provided above.

Figure 5:
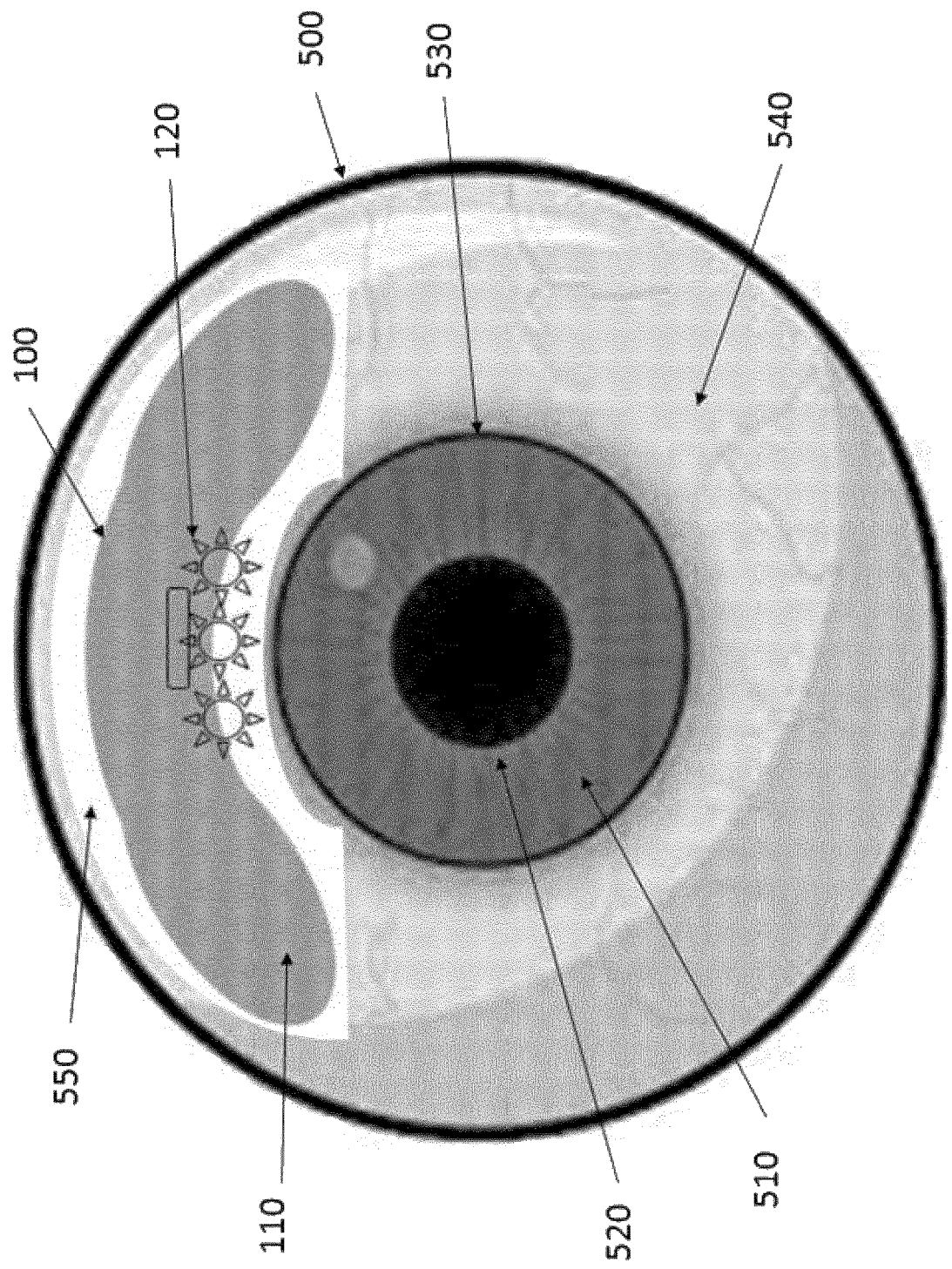
FIG. 5 illustrates a schematic front view of an eye (eyelid not shown) on which the ocular device of FIG. 1 is positioned.

FIG. 5 illustrates a schematic front view of an eye 500 (with the eyelid removed for clarity) illustrating the location of the ocular device 100 in relation to the iris 510, the pupil 520, the cornea 530, the sclera 540 and the upper fornix 550. The ocular device 100 is shown positioned in the upper fornix 550 of the eye 500 over the sclera 540. As shown, the light source 120 is activated to direct light through the cornea 530, into the pupil 520 and onto the retina (not shown).

Figure 6:
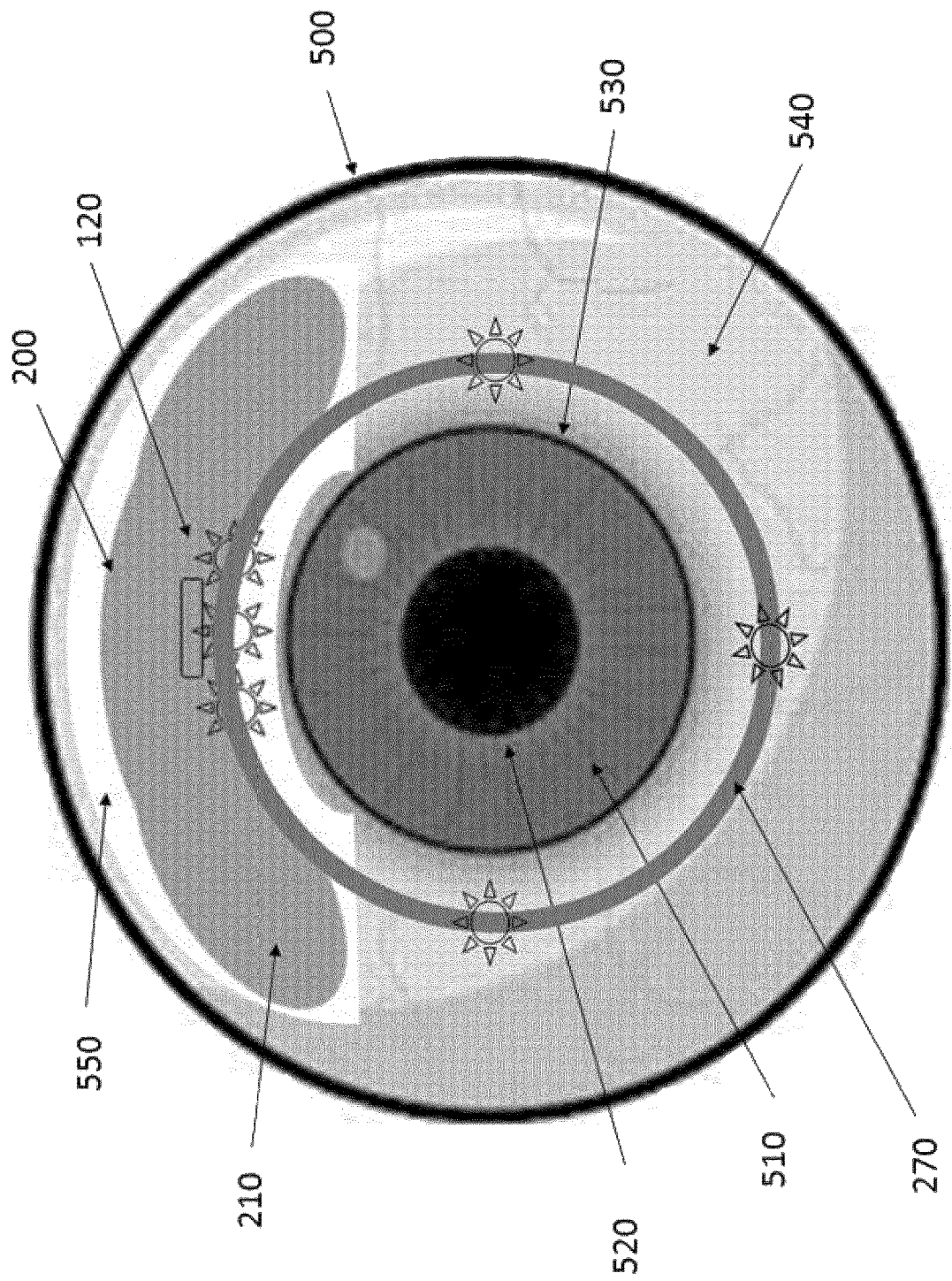
FIG. 6 illustrates a schematic front view of an eye (eyelid not shown) on which the ocular device of FIGS. 2 and 3 is positioned.

FIG. 6 is similar to FIG. 5 but illustrating the placement of the ocular device 200 on the eye 500. As before, the ocular device 200 is positioned in the upper fornix 550 of the eye 500 with the ring extension 270 extending around the cornea 530 on the conjunctiva over the sclera 540. As shown, the light source 120 is activated to direct light around the ring extension 270, through the cornea 530, into the pupil 520 and onto the retina (not shown).

It will readily be appreciated that the ocular device 300 of FIG. 3 would be positioned on the eye in the same way as the ocular device 210 as shown in FIG. 6.

Figure 7:
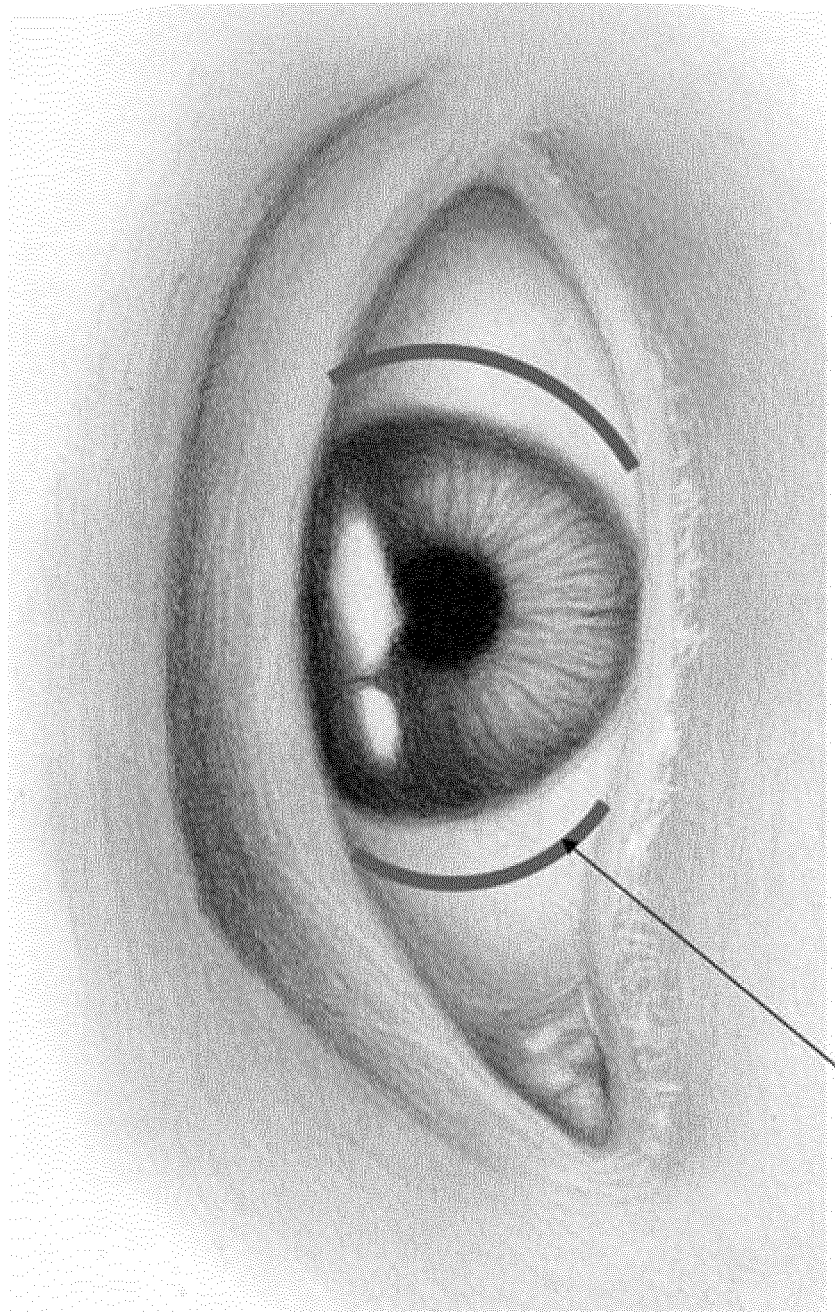
FIG. 7 illustrates a schematic front view of an eye on which the ocular device of FIGS. 2 and 3 is positioned.

The ring extension 270 of the ocular devices 200, 300 of FIGS. 2 and 3 is shown in FIG. 7 as a partially visible ring around the cornea when eye is open, the ring being emphasized in FIG. 7 for clarity. As described above, the ring is at least partially transparent to be able to direct light into the eye and toward the retina.

In-vitro and in-vivo studies with prototypes of the ocular device of the present invention have shown that a light emitted from the upper fornix location (down towards the cornea) indirectly refracts through cornea surface via reflection from the waveguide created by the combination of the conjunctival sac (upper eyelid inner surface and scleral surface), cornea surface, tear film, and device thickness before entering pupil to reach retina. This means that the channel for guiding light towards the retina is assisted and augmented by the device itself.

It will readily be appreciated that the ocular devices described above form part of an ocular system with a suitable recharger or base station for at least recharging the device where an internal energy source is provided. In one embodiment, the recharger or base station comprises a receptacle or storage compartment for storing/recharging/programming the ocular device when not in use. In another embodiment, the recharger or base station comprises a compartment for storing/recharging/programming a headband associated with the ocular device, the ocular device being stored in a separate storage compartment when not in use. These embodiments are described in more detail with reference to FIGS. 8 and 9 below. In both embodiments, the recharger station uses near-field induction for transferring data to and from the ocular device or headband and for charging the ocular device or headband.

Figure 8:
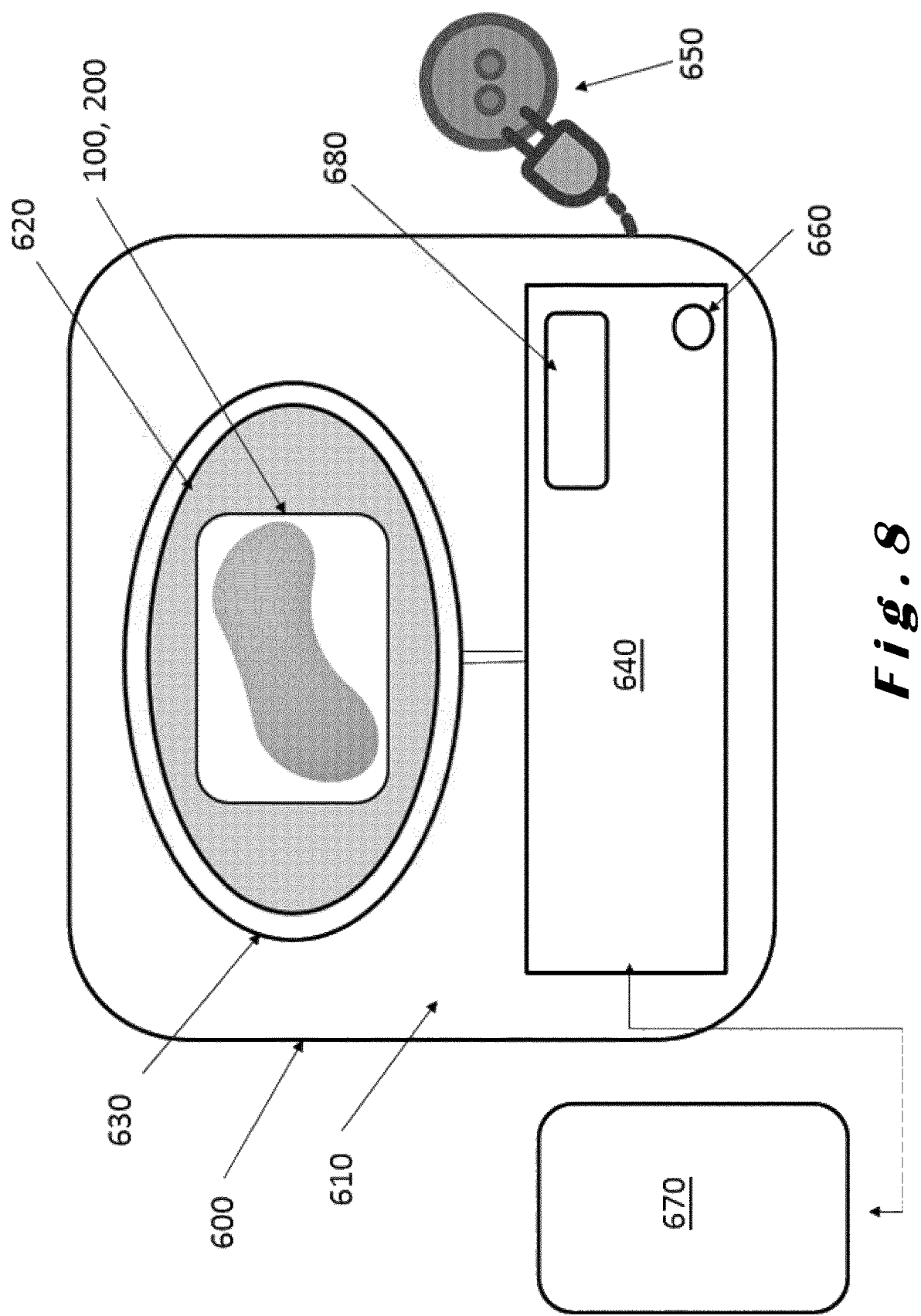
FIG. 8 illustrates schematically a base station for use with the ocular device of FIGS. 1 and 2.

Turning now to FIG. 8, a base station 600 is shown which comprises a housing 610 in which a receptacle 620 is provided for storing, cleaning, recharging and programming the ocular devices 100, 200 of FIGS. 1 and 2. The receptacle 620 may comprise a removable and replaceable contact lens case or the like. Around the receptacle 620 is located an antenna or coil 630 by way of which the ocular devices 100, 200 can be recharged and re-programmed as necessary. As shown, the antenna or coil 630 is connected to a microcontroller 640 also provided within the housing 610. The base station 600 is connectable to a main power supply (e.g. a standard 110V/220V electrical outlet) as indicated by power cable 650 and includes an LED indicator 660 which indicates the status, that is, "recharging" and/or "ready".

The microcontroller 640 is also connectable to a computer 670 for receiving programming instructions therefrom. In addition, the microcontroller 640 transfers readings from the ocular devices 100, 200 to the computer 670. The connection between the microcontroller 640 and the computer 670 may be wired via a USB cable or wireless using known wireless technologies, such as, Wi-Fi (a trademark of the Wi-Fi Alliance) and Bluetooth (a trademark of the Bluetooth Special Interest Group). The computer 670 may also provide charging for the base station 600 by way of a USB cable.

The computer may comprise a desktop computer or a more portable device, for example, a laptop, a tablet, a smartphone or similar devices.

Once in the base station 600, the ocular device 100, 200 can be calibrated to ensure that the light sensor emits the correct wavelength and luminosity for a predetermined period of time, for example, 4 weeks.

Figure 9:
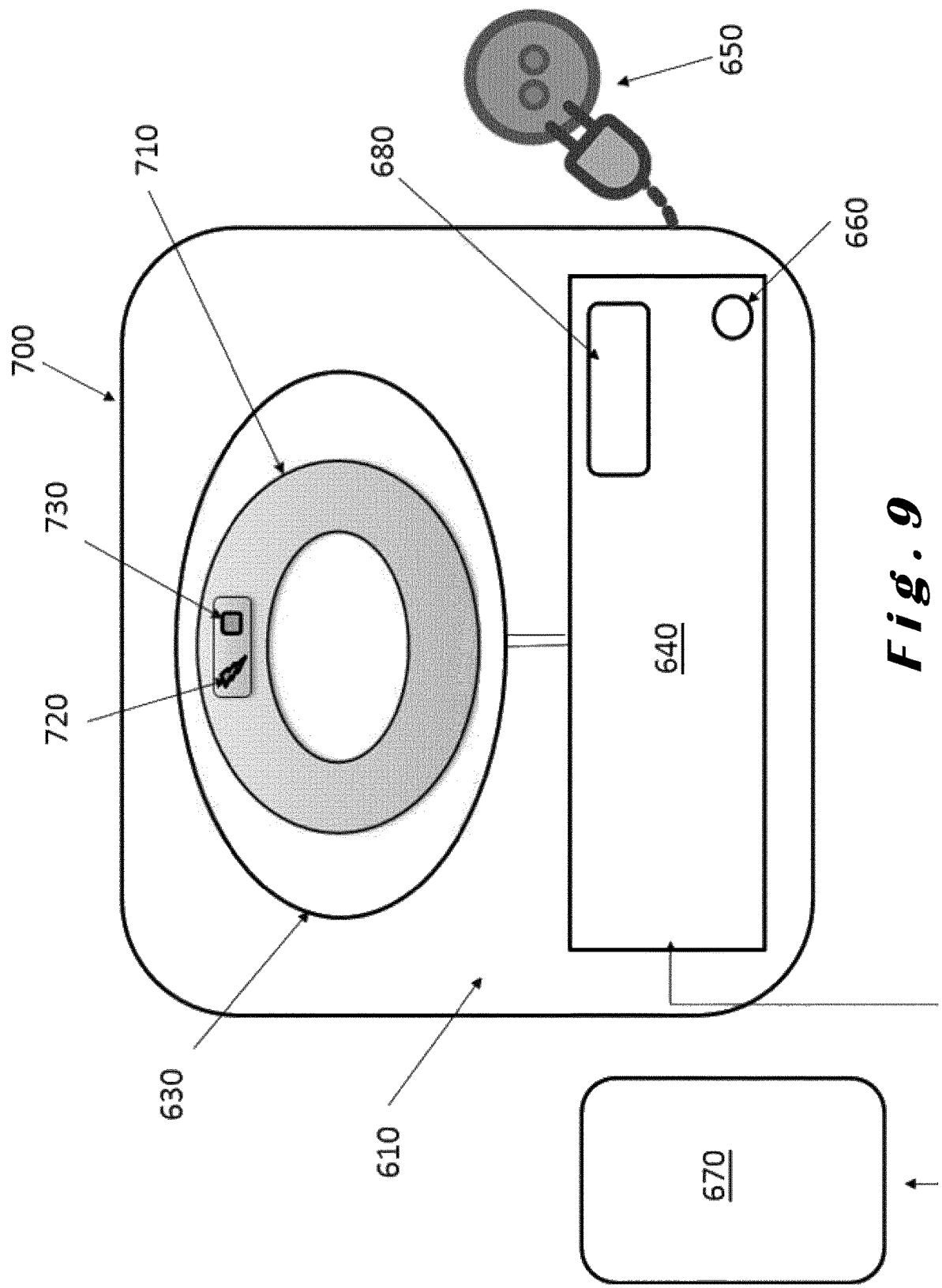
FIG. 9 illustrates schematically a base station for use with the ocular device of FIG. 3.

FIG. 9 shows a base station 700 which is similar to the base station 600 shown in FIG. 8 but which is used for charging a headband or eye mask 710 having an embedded energy source 720 and an embedded antenna 730 which is used in conjunction with the ocular device 300. Components of the base station 700 which are common to the base station 600 will not be described again here.

The headband or eye mask 710 comprises at least one eye patch in which the antenna 730 forms a part. It will readily be understood that it is possible to configure the headband or eye mask 710 to accommodate two eye patches, one for each eye, and to include separate embedded energy sources which power individual ocular devices. The headband or eye mask 710 is used at the same time as the ocular device 300, the headband/eye mask forming the external energy source for the ocular device. In use, the embedded energy source 720 powers the microcontroller 140 and the light source 120 in the ocular device 300 through inductive coupling between the embedded antenna 730 in the eye patch and the antenna 250 located in the ring extension 270 of the ocular device 300.

For recharging and/or programming, the headband or eye mask 710 is positioned inside the antenna or coil 630. Recharging of the embedded energy source 720 is achieved via inductive coupling between the embedded antenna 730 in the headband and the antennal or coil 630 of the base station 700. In addition, the headband or eye mask 710 may include a memory (not shown) which is accessible by the ocular device 300 via the antenna 250 for receiving programming from the computer 670 via the microcontroller 640 and the antenna or coil 630 and/or transferring data to the computer 670 from the ocular device 300 via the antenna 250 and antenna or coil 630.

In this embodiment, the ocular device 300 is stored in a storage container (not shown) in a similar way to a contact lens. The container may also be used for cleaning the ocular device whilst it is being stored.

As described above, the headband or eye mask 710 effectively forms a mini-charger unit. In alternative embodiments, the headband or eye mask 710 may be replaced by a spectacle frame (not shown) which either incorporates the mini-charger unit or can have the mini-charger unit mounted thereto.

The ocular system as described above may be used for the treatment of ocular hypertension using directed light programmed to have a primary light spectrum peak in the green region which can be adjusted to provide retinal illuminance of predetermined intensity and time, for example, up to 100 scotopic Td for a treatment time of up to 15 minutes per hour.

In addition, other disorders of the eye may be treated using light therapy, for example, diabetic retinopathy, diabetic macular oedema and/or age-related macular degeneration and other related retinopathies. In these cases, therapy to reduce oxygen demand is needed to prevent hypoxia and low-level light therapy (LLLT) especially during the course of the night (during sleep) can be beneficial. In each case, similar light therapy as for ocular hypertension can be used as described above.

Figure 10:
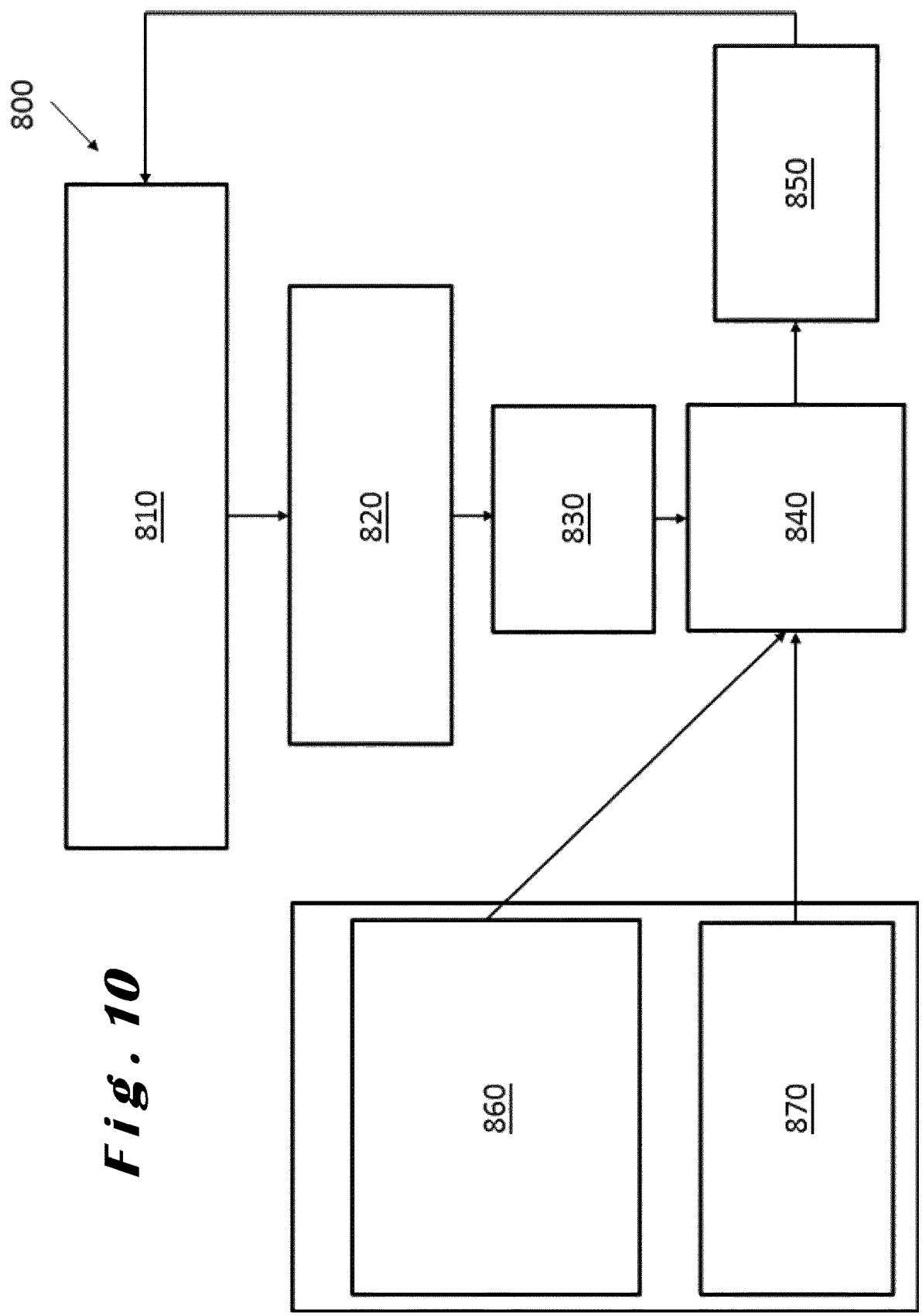
FIG. 10 illustrates a flow chart showing how to use the ocular device of FIGS. 1 and 2.

FIG. 10 illustrates a flow chart 800 for use of the ocular device 100, 200 described above with reference to FIGS. 1 and 2. Starting from the ocular device in its base station (as described above with reference to FIG. 8), the device is removed from the base station (step 810) and activated for use (step 820). In some embodiments, the device auto-activates when removed from the base station. The device is then placed in the upper fornix of an eye of a user (step 830) and the pre-programmed light therapy is applied to the eye (step 840). The device is then removed from the eye and returned to the base station (step 850). Optional steps whilst the device is in the upper fornix of the eye include measuring and recording eye motion using a sensor, for example, an accelerometer as described above, to determine adherence to the use of the device and other data related to improving the therapy (step 860), as well as determining other data to improve the therapy, for example, using further sensors to measure the light output from the light source etc. (step 870). In addition, in step 860, temperature may be measured as another or additional way of determining adherence to the therapy regimen.

Figure 11:
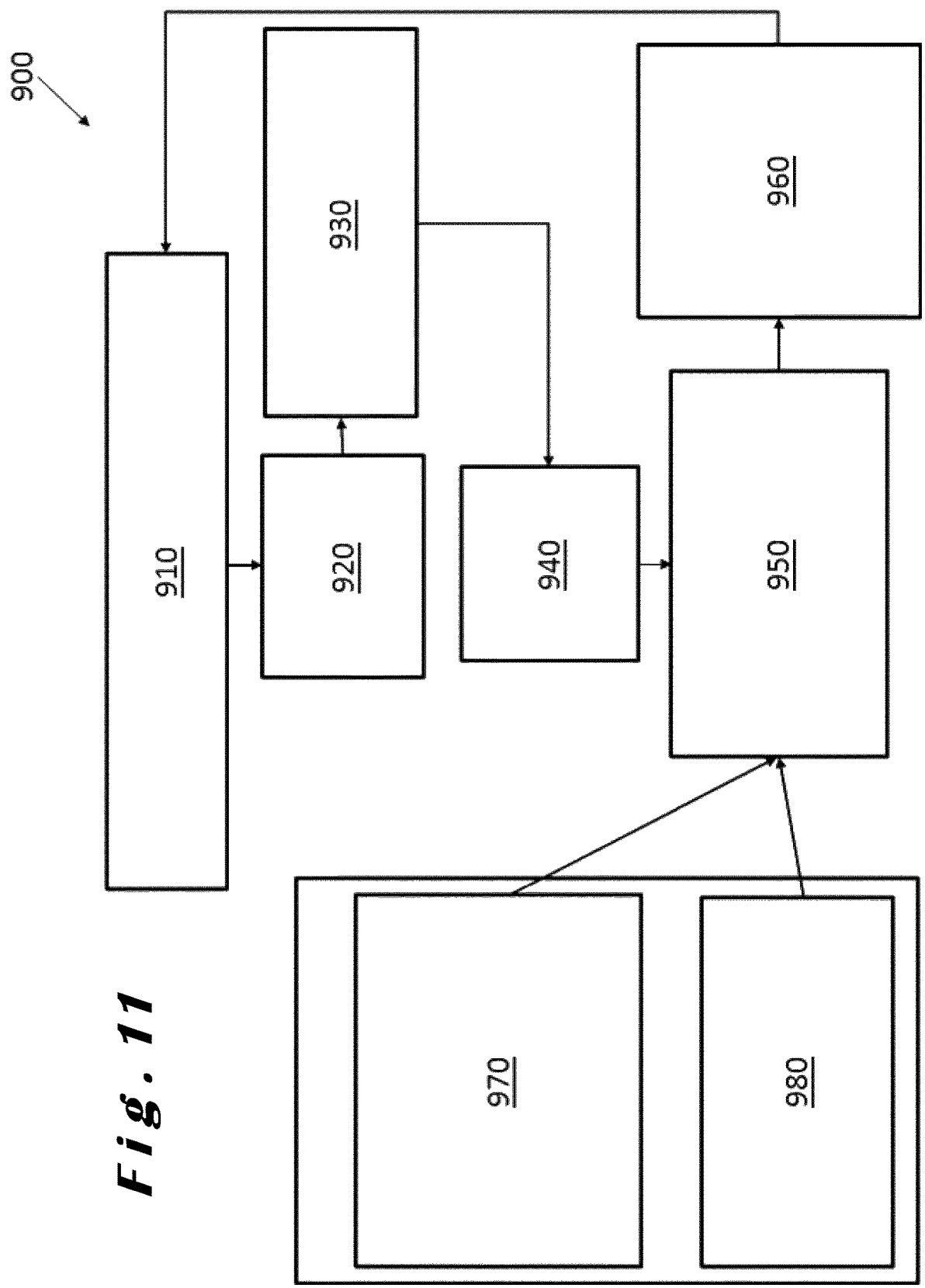
FIG. 11 illustrates a flow chart shown how to use the ocular device of FIG. 3.

FIG. 11 illustrates a flow chart 900 for use of the ocular device 300 described above with reference to FIG. 3. Starting from the ocular device in its base station (as described above with reference to FIG. 9), the device is removed from the storage container (step 910) and placed in the upper fornix of an eye of a user (step 920). The associated headband is removed from its base station (described above with reference to FIG. 9) and is positioned on the head of the user with the eyepatch coil located over the eye in which the ocular device has been positioned (step 930). The ocular device is activated using the headband (step 940) and the pre-programmed light therapy is applied to the eye using inductive power coupling of the eye patch coil and the antenna in the ring extension of the ocular device (step 950). The headband is removed from the head and the ocular device is then removed from the eye, the headband being returned to the base station and the ocular device to its storage container (step 960). Optional steps whilst the device is in the upper fornix of the eye include measuring and recording eye motion using a sensor, for example, an accelerometer as described above, to determine adherence to the use of the device and other data related to improving the therapy (step 970), as well as determining other data to improve the therapy, for example, using further sensors to measure the light output from the light source etc. (step 980). In addition, in step 970, temperature may be measured as another or additional way of determining adherence to the therapy regimen.

Figure 12:
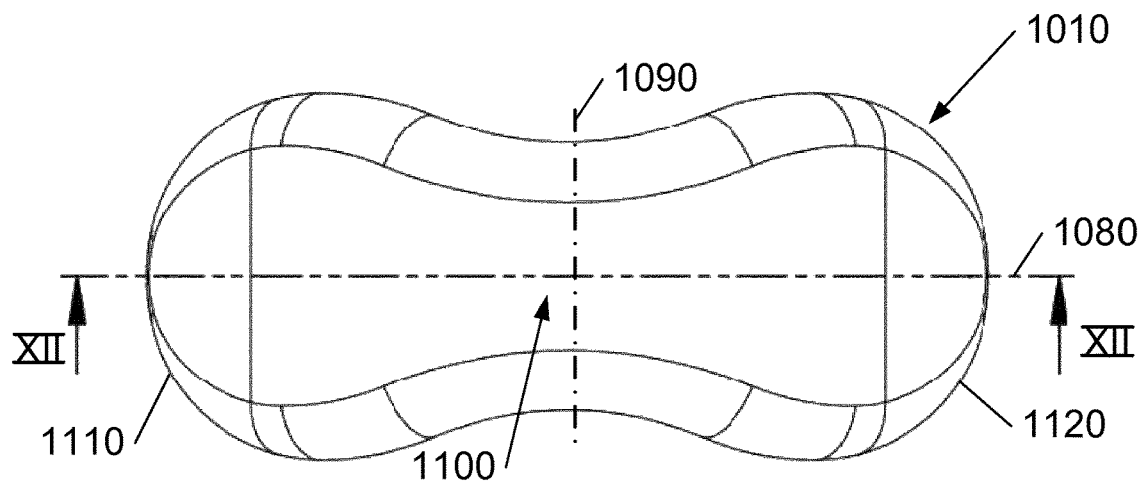
FIG. 12 illustrates a schematic top view of an embodiment of a housing or body component of an ocular device in accordance with the present invention.
Figure 13:
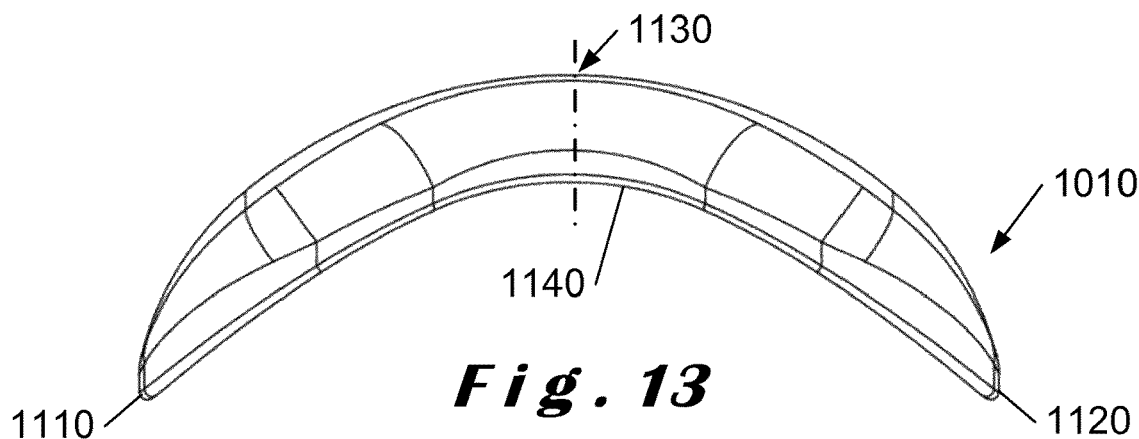
FIG. 13 illustrates a schematic side view of the housing shown in FIG. 12.
Figure 14:
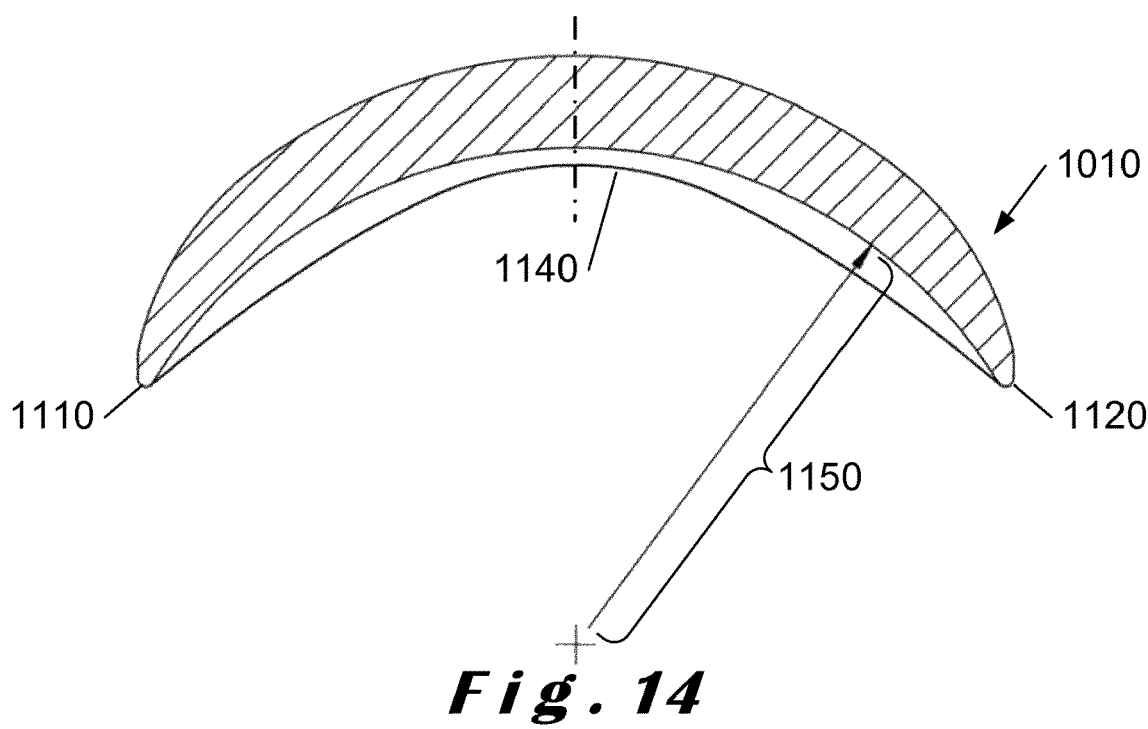
FIG. 14 illustrates a sectioned view of FIG. 12 taken on lines XII-XII.

An exemplary embodiment of a housing or body portion 1010 in accordance with the present invention is shown in FIGS. 12 to 14. The housing or body component 1010 is symmetrical about a longitudinal axis 1080 and about a transverse axis 1090, and, has a base radius of 12.5 mm (shown as 1150 in FIG. 14) with an overall length, from end to end, of 21 mm (FIG. 13). The thickness of the housing or body component 1010 is 2.3 mm in its central region 1100 tapering towards its longitudinal edges 1110 and 1120 (that is, along the length of the housing or body component). The width of the central region 1100 is 7 mm extending to 10 mm adjacent the longitudinal edges 1110 and 1120. As shown, the housing or body component 1010 is contoured and has a different radius (corresponding to the basic radius) for its upper surface 1130 when compared to its lower surface 1140.

In another embodiment, the thickness and/or width of the housing or body component may be substantially constant along its entire length.

Figure 15A:
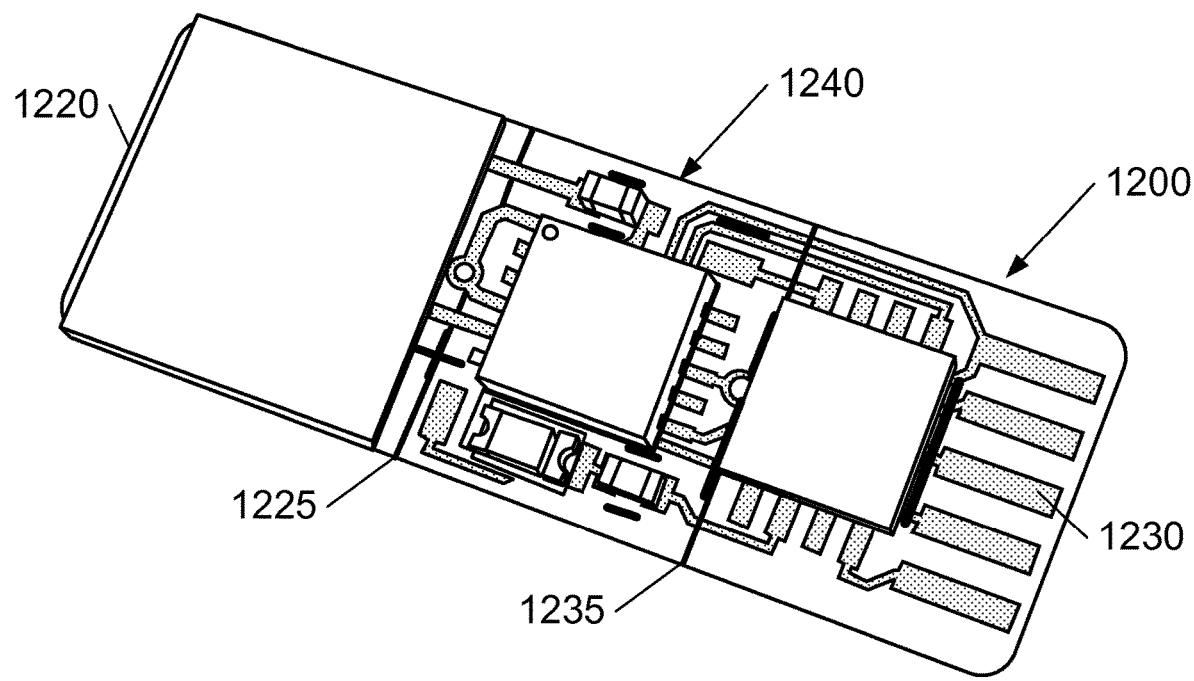
FIGS. 15a and 15b illustrate respective front and back sides of a flexible printed circuit board in accordance with the present invention.
Figure 15B:
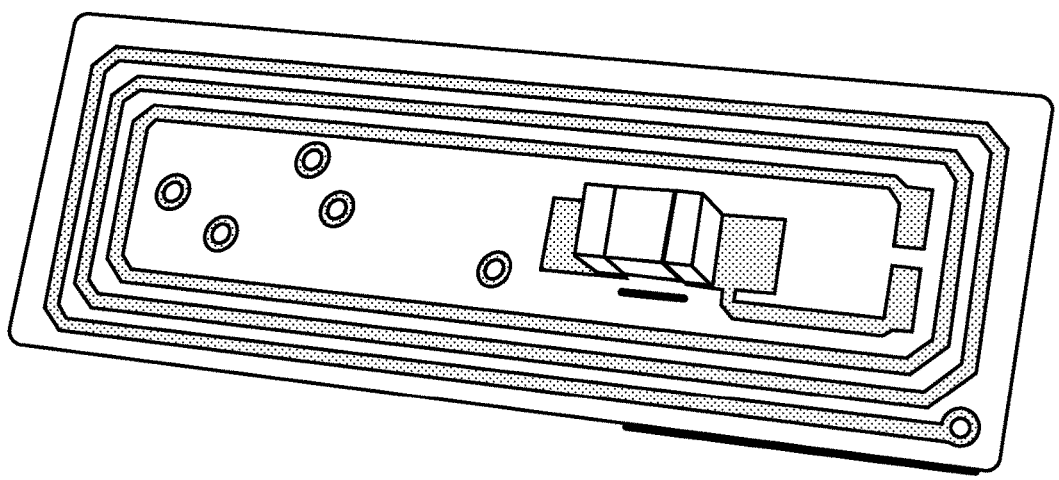

FIGS. 15a and 15b illustrate one example of a flexible printed circuit board (PCB) 1200 in accordance with the present invention. As shown, the PCB 1200 comprises three sections: a central section 1210 and two side sections 1220 and 1230. Each of the two side sections 1220 and 1230 is hinged to the central section 1210 as shown at 1225 and 1235 respectively. The term "hinged" as used herein is intended to refer to the flexibility of the PCB and does not mean that there is any disconnection between the sections thereof but that portions of the PCB are thinner to allow "hinging" between the main sections thereof to provide the flexibility required for handling of the device when being inserted and removed from its location on the scleral surface. Although electronic components are shown on the PCB 1200, they are not referenced for clarity.

For example, the electronic components may comprise a lithium-based battery as a main power supply unit for delivering electrical power to all the embedded components on the PCB. A voltage regulator may be provided to ensure that the correct level of electrical power is delivered to the components. The battery may periodically be recharged through a radio frequency identification (RFID) antenna located on the bottom side of the PCB. The voltage induced at the ends of the RFID antenna is rectified and limited so that it can recharge the battery.

Integrated chips (ICs) may be used to implement the microcontroller and an RFID chip associated with the antenna. Various capacitors and resistors may be provided for regulating the power supplied to a light-emitting diode which provides the therapeutic light for delivery to the retina.

In the illustrated embodiment, the sections are of different sizes, but it will readily be appreciated that each section may be dimensioned in accordance with the housing or body component in which it is to be mounted.

For example, the central section may have a length of between 4 mm and 8 mm with two side sections having equal lengths of approximately 7 mm. It will readily be appreciated that other dimensions may be possible and such dimensions will be determined by the thickness of the housing or body component. In another embodiment, the sections may be dimensioned differently with a central section of between 4 mm and 6 mm, one side section of 5 mm and the other side section of approximately 7 mm. In this embodiment, the central section may be offset from the transverse axis 1090 (as shown in FIG. 12) by between 1 mm and 2 mm. It will readily be understood that these dimensions are by way of example only, and are not limiting.

Figure 16:
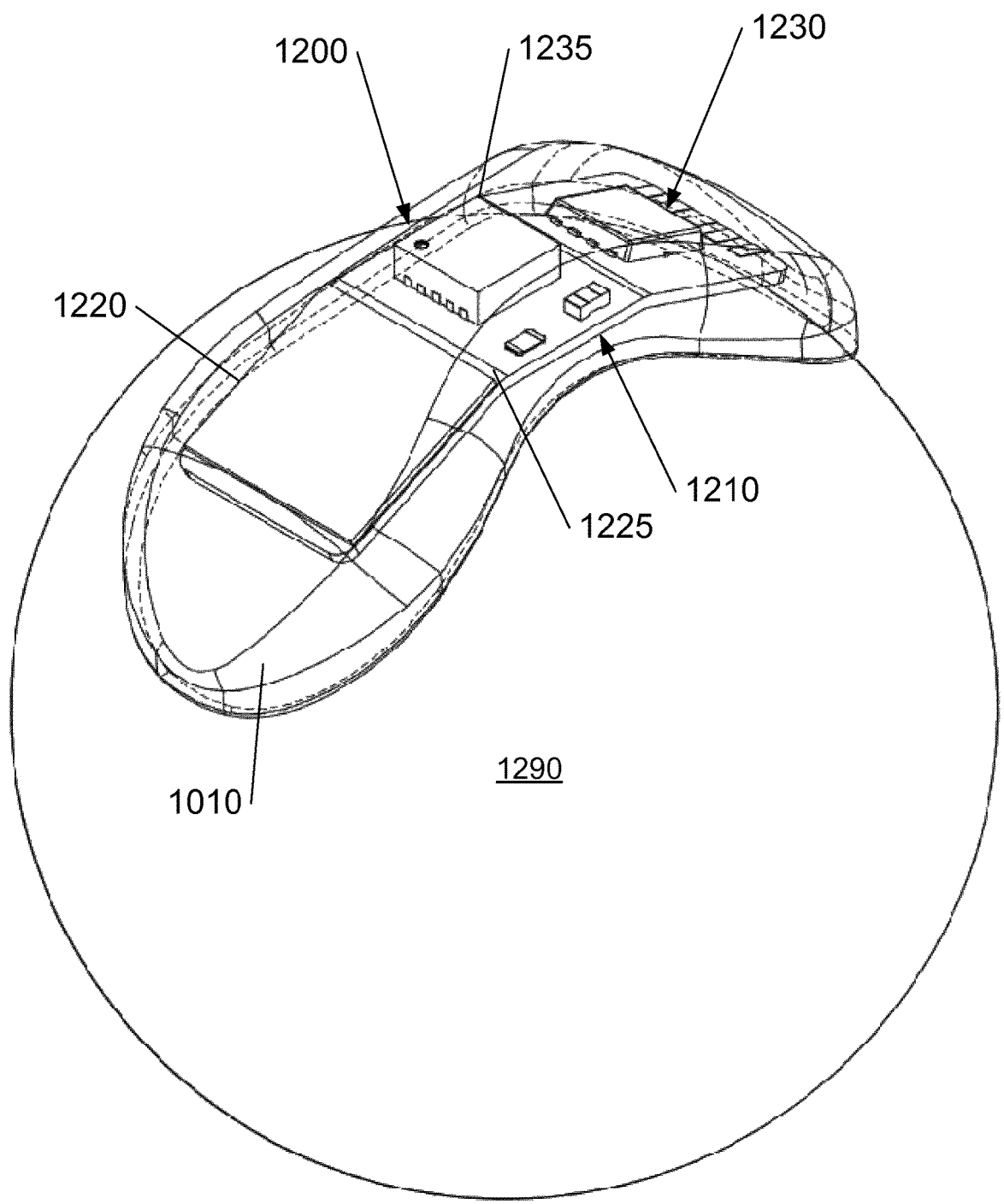
FIG. 16 illustrates a perspective view of a printed flexible circuit board similar to that shown in FIGS. 15a and 15b inside the housing shown in FIGS. 12 to 14 positioned on a representation of an eyeball.

FIG. 16 illustrates an assembled flexible PCB 1200 (FIGS. 15a and 15b) within a housing or body component 1010 (FIGS. 12 to 14) and positioned on a representation 1290 of an eyeball. It will readily be appreciated that FIG. 16 is representative of an ocular device and it may not be possible to see the PCB 1200 through the housing or body component 1010 depending on the material from which the housing or body component is made.

Although the ocular devices and ocular systems of present invention have been described for use solely as light therapy, it will readily be appreciated that the light can be used in conjunction with other conventional therapies, such as, drug treatments. For example, a periodic wavelength, that is, blue light (470 nm), corresponding to an activation waveband of a photo-pharmaceutical compound (chemotherapy drug) disposed at a treatment site within the eye can be provided by these ocular devices for treating eye cancers.

The programmable light source may act as an on/off switch (e.g. blue light on, orange light off) to stimulate or suppress neural activity in specific neural cells containing light sensitive proteins (field of optogenetics) for the treatment of schizophrenia, Parkinson's, Alzheimer's, epilepsy, narcolepsy, pain management, and certain eye diseases and disorders. Optogenetics originated as an effort to control neural function with genetically encoded photoreceptors that use abundant chromophores, for example, retinal chromophores, but now it covers a variety of cellular functions which have revolutionized the control of biological pathways in neuroscience. Optogenetic microdevices have been implemented as described in an article entitled "Evolution of optogenetic microdevices" by Kale, R P et al., Neurophotonics, 2015.

As discussed above, the ocular device may emit a periodic wavelength in the red to near infrared regions of the electromagnetic spectrum, for example, using wavelengths between 620 nm and 3000 nm for warming of the Meibomian gland in the upper eyelid as a treatment for MGD and related dry eye syndromes especially during the night-sleep period. Here, the ocular side of device is coated with a shield to limit energy from entering eye (inward direction) or a reflecting layer to emit energy in only the outward direction (toward the Meibomian gland).

The ocular devices may also emit a periodic or one time per day (e.g. a 15- to 30-minute morning session as a form of "dawn simulation" therapy) wavelength as a treatment for reducing depressive symptoms, such as, seasonal affective disorder (SAD), major depressive disorder (MDD), bipolar affective disorder, and atypical depression.

In addition, light therapy may also be used as a treatment for sleep disorders including or associated with Circadian rhythm problems, narcolepsy, jet-lag, work-shift changes, etc.

The ocular devices as described above have the following advantages:

The housing of the ocular device has a base curve designed to be used on the bulbar or ocular conjunctiva in the upper fornix (and not on the cornea) for more universal fit and enhanced comfort. This is in contrast to the use of contact lenses which are positioned on the cornea.

A sensor (for example, an accelerometer or a strain gauge) can be used to record eye globe movement to ensure patient adherence to therapy. Such a sensor also provides other valuable data such as recording different stages of sleep and duration, for example, rapid eye movement (REM) sleep.

Hybrid technologies may be employed for light energy efficiency, for example a fluorescent and light-emitting diode combination.

The ocular device may incorporate thin film energy technology, micro LED technology and wireless rechargeable features into a very small housing. One or more thin film energy harvesting cells may be used to harvest kinetic energy derived from eye-device movement during Rapid Eye Movement (REM) sleep cycles as well as during blinking.

As described above, the ocular devices shown in FIGS. 1 and 2 can simultaneously be cleaned and recharged so that the device can be used every day.

The ocular device of FIG. 1 is effectively invisible as it is located under and hidden by the eyelid. For the ocular device of FIG. 2, only the ring extension is visible when the device is worn as shown in FIG. 7.

Emitted light from the device is efficiently contained within the eye itself. It is reflected, refracted, scattered, and diffracted as it propagates along the light guiding channel created by device, tear film, and conjunctival sac walls as it makes its way through the cornea and pupil until it reaches retina.

The ocular devices are more energy efficient as there is no need for light to pass from a source outside the body component through a closed eyelid.

The risk of having too much light entering the eye during therapy is eliminated (daytime usage).

The ocular devices and ocular systems described above address the concerns and limitations in the prior art to provide the following potential benefits:

The use of such ocular devices and systems are non-invasive as no surgery or incisions are required, as the ocular device being introduced into the upper fornix of the eye.

The devices can be used with non-toxic therapy (i.e. with no drugs) if simply light therapy is required. As described above, these devices may also be used with drug therapy.

There are no pharmacological side effects (i.e. no pain, staining, itching due to toxins or preservatives).

There is no requirement for bulky and rigid components placed on nose or face (like goggles or glasses which general have rigid plastic assemblies) for the ocular device shown in FIGS. 1 and 2.

Each device is programmable for personalized treatment.

As the device is worn under the eyelid, there is no negative aesthetic impact, thus increasing patient adherence/acceptance rate.

The ocular device can readily be positioned and removed without medical intervention, and, is convenient to use.

It is possible to wear the device for multiple days and weeks as there is no need for daily removal (provided the device is either externally powered or can be powered remotely).

As the device makes no corneal contact, it is generally more safe and comfortable to wear providing maximum safety, comfort and wear time.

The ocular device is removable (and replaceable) at will.

It is rechargeable (i.e. it has a rechargeable power source).

The device can operate wirelessly as it uses rechargeable battery or an external power source.

Advantages over smart contact lens approaches include:

The device is not intended to reside on the over-sensitive, highly innervated corneal surface for maximum safety and comfort.

As the device does not cover the corneal surface, it does not limit the oxygen supply to the cornea—especially during long wear times.

The device is aesthetically neutral as it is hidden under eyelid for no negative impact to appearance.

There is no need for specific base and skirt curves (custom sizes for each patient or group of patients) for a proper fit as one size fits all.

There is no compromise of vision during use and does not cause blurring, nausea, headaches, imbalance or dizziness.

The ocular device allows a patient or user to continue to wear normal prescription glasses or corneal contact lenses (for example, gas permeable or rigid contact lenses).

There is no possibility of damage or remodeling of the corneal surface affecting post-wear vision.

The device is portable and provides a user with full mobility as it can be used anywhere including at home and when traveling.

The device provides an adaptable platform for additional low-level light therapies (LLLT) for other diseases and disorders.

The ocular device can readily be used with a smart phone and can be Bluetooth enabled and controlled.

The invention claimed is:

1. An ocular device configured to be worn on a scleral surface of an eye of a user, the device comprising: a body component;
at least one light source component mounted in the body component and configured for providing light energy to an eye;
a microcontroller component mounted in the body component and configured for controlling the operation of at least the light source component;
an antenna component at least partially mounted in the body component and connected to the microcontroller component, the antenna component being configured for at least receiving external signals and for passing them to the microcontroller component;
at least one energy source component configured for supplying power to at least the light source component and the microcontroller component; and
at least one flexible printed circuit board mounted in the body component, at least one of said at least one light source component, the microcontroller component, and said at least one energy source component being mounted thereon;
wherein said body component is configured to be positioned in an upper fornix of the eye of a user such that the base curvature of the ocular device is configured to correspond to the curvature of the scleral surface of the eye:
wherein said at least one flexible printed circuit board comprises a plurality of sections hinged relative to one another; and
wherein the plurality of sections comprises a central section and two side sections.

2. An ocular device according to claim 1, further comprising:
a substantially hollow ring extension which extends from the body component.

3. An ocular device according to claim 2, wherein the ring extension comprises a waveguide configured for directing light energy from the at least one light source.

4. An ocular device according to claim 3, wherein the ring extension comprises the antenna component.

5. An ocular device according to claim 1, wherein the antenna component is mounted on said at least one flexible printed circuit board.

6. An ocular device according to claim 1, wherein the energy source component is mounted within the body component and comprises at least one thin-film rechargeable micro-battery.

7. An ocular device according to claim 1, wherein the energy source component is external to the body component and is configured to couple with the antenna component to provide energy thereto for powering at least one light source component and the microcontroller component.

8. An ocular device according to claim 1, further comprising
a sensor component mounted on said at least one flexible printed circuit board in the body component.

9. An ocular device according to claim 1, wherein the light source component comprises one or more of:
at least one solid-state light-emitting diode;
at least one organic light-emitting diode;
at least one quantum dot light-emitting diode;
a phosphorescent light source;
a chemiluminescent light source; and
strontium aluminate nanoparticles.

10. An ocular device according to claim 1, wherein the light source component emits light in a wavelength range of 430 nm to 590 nm and a luminous flux of up to 10 lm.

11. An ocular device according to claim 1, wherein the light source component is programmable.

12. An ocular device according to claim 1, wherein the microcontroller component comprises a wireless module configured for communicating wirelessly with an external controller, the external controller being configured for at least programming the microcontroller to control the light source.

13. An ocular device according to claim 12, wherein the external controller is configured for controlling at least one of:
the wavelength;
light patterns;
duration of the light generated by the light source component; and
luminosity of the light generated by the light source component.

14. An ocular device according to claim 1, wherein the antenna component interfaces with a recharger station and is configured to recharge the energy source component.

15. An ocular device according to claim 1, further comprising:
at least one further sensor component configured to measure at least one of the luminance of the light source component and temperature of the ocular device, and to monitor parameters indicative of at least one of: use and performance of the device, and physiological conditions of the eye; and
wherein the microcontroller component includes a memory component which is configured to store data measured by the at least one further sensor component.

16. An ocular device according to claim 1, wherein the body component comprises a soft, flexible, conforming, biocompatible material which encompasses all components of the device, wherein the biocompatible material comprises a hydrophilic-treated silicone rubber; and
wherein the body component is configured for treatment of its outer surface with an anti-microbial coating.

17. An ocular device according to claim 16, wherein the body component includes at least one portion which comprises one or more of:
a solid screen for at least inhibiting light from passing through that portion; and
at least one surface coated with a reflector mirror film.

18. An ocular device according to claim 16, wherein the body component comprises at least one kinetic energy harvesting cell connected to the energy source component.

19. An ocular system, comprising:
an ocular device configured to be worn on a scleral surface of an eye of a user, the device comprising a body component configured to be positioned in an upper fornix of the eve such that the base curvature of the ocular device is configured to correspond to the curvature of the scleral surface of the eye;
at least one light source component mounted in the body component and configured for providing light energy to an eye;
a microcontroller component mounted in the body component and configured for controlling the operation of at least the light source component;
an antenna component at least partially mounted in the body component and connected to the microcontroller component, the antenna component being configured for at least receiving
external signals and for passing them to the microcontroller component;
at least one energy source component configured for supplying power to at least the light source component and the microcontroller component; and
a recharger station for recharging the energy source component of the ocular device.

20. An ocular system according to claim 19, wherein the recharger station comprises a storage container into which the ocular device is placed and submerged in a cleaning solution when not in use, wherein the energy source component is recharged and the recharger station transfers data to and from the ocular device, when in the storage container.

21. An ocular system according to claim 19, wherein the recharger station comprises a mini-charger control unit configured to form part of an eye mask wearable by a user of the ocular device.

22. A method of reducing intraocular pressure and/or ocular
hypertension, the method comprising:
inserting an ocular device onto an ocular conjunctiva of an eye and under an eyelid of a user; and
directing light into the eye of the user from the ocular device;
wherein the ocular device is configured to be worn on a scleral surface of an eye of a user and comprises:
a body component configured to be positioned in an upper fornix of the eve of the user such that the base curvature of the ocular device is configured to correspond to the curvature of the scleral surface of the eye:
at least one light source component mounted in the body component and configured for providing light energy to an eye;
a microcontroller component mounted in the body component and configured for controlling the operation of at least the light source component;
an antenna component at least partially mounted in the body component and connected to the microcontroller component, the antenna component being configured for at least receiving external signals and for passing them to the microcontroller component; and
at least one energy source component configured for supplying power to at least the light source component and the microcontroller component.

23. The method of claim 22, further comprising:
adjusting the light to have a retinal illuminance of up to 100 scotopic Td for a treatment time of up to 15 minutes per hour.

24. A method of reducing retinal hypoxia in the treatment of diabetic retinopathy or age-related macular degeneration, the method comprising:
inserting an ocular device onto an ocular conjunctiva of an eye and under an eyelid of a user; and
directing light into the eye of the user from the ocular device; and
wherein the ocular device is configured to be worn on a scleral surface of an eye of a user and comprises:
a body component configured to be positioned in an upper fornix of the eye of the user such that the base curvature of the ocular device is configured to correspond to the curvature of the scleral surface of the eye;
at least one light source component mounted in the body component and configured for providing light energy to an eye;
a microcontroller component mounted in the body component and configured for controlling the operation of at least the light source component;
an antenna component at least partially mounted in the body component and connected to the microcontroller component, the antenna component being configured for at least receiving external signals and for passing them to the microcontroller component; and
at least one energy source component configured for supplying power to at least the light source component and the microcontroller component.

25. The method of claim 24, further comprising:
adjusting the light to have a retinal illuminance of up to 100 scotopic Td for a treatment time of up to 15 minutes per hour.

* * * * *